US007288402B2

(12) United States Patent
Osswald et al.

(10) Patent No.: US 7,288,402 B2
(45) Date of Patent: Oct. 30, 2007

(54) RHODOCOCCUS NITRILE HYDRATASE

(75) Inventors: Steffen Osswald, Rodenbach (DE); Stefan Verseck, Hanau (DE); Uta Deiting, Frankfurt (DE); Christoph Weckbecker, Gründau-Lieblos (DE); Klaus Huthmacher, Gelnhausen (DE); Michael Binder, Hasselroth-Niedermittlau (DE); Maria-Regina Kula, München (DE); Konrad Odendahl, Köln (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/083,327

(22) Filed: Mar. 18, 2005

(65) Prior Publication Data

US 2006/0068467 A1    Mar. 30, 2006

(30) Foreign Application Priority Data

Mar. 20, 2004   (DE)  ..................... 10 2004 013 824

(51) Int. Cl.
*C12N 9/80* (2006.01)
*C12N 9/08* (2006.01)
*C07H 21/04* (2006.01)
*C12P 21/06* (2006.01)
*C12P 13/02* (2006.01)

(52) U.S. Cl. ..................... 435/228; 435/129; 435/69.1; 435/252.2; 435/471; 435/320.1; 435/252.3; 435/252.33; 536/23.2

(58) Field of Classification Search ............... 435/69.1, 435/128, 252, 471; 536/23.2
See application file for complete search history.

(56) References Cited

U.S. PATENT DOCUMENTS 5,807,730 A * 9/1998 Ito et al. ..................... 435/232
2004/0142447 A1   7/2004 Robins et al. ............... 435/227

FOREIGN PATENT DOCUMENTS

| DE | 101 55 928 | 11/2001 |
|---|---|---|
| EP | 0 362 829 | 7/1995 |
| EP | 0 790 310 | 8/1997 |
| EP | 1 055 724 | 11/2000 |
| JP | 5-284982 | 11/1993 |
| WO | WO/98/32872 | 7/1998 |
| WO | WO 01/60789 | 8/2001 |
| WO | WO 02/055670 | 7/2002 |
| WO | WO 02/070717 | 9/2002 |

OTHER PUBLICATIONS

Shimizu et al. Accession No. E 13809, (JP 1997234075, Sep. 9, 1997).*
Brady, et al., "Characterisation of Nitrilase and Nitrile Hydratase Biocatalytic Systems," *Appl. Microbiol. Biotechnol. 64* :76-85 (2004).
Ingvorsen, et al., "Microbial Hydrolysis of Organic Nitriles and Amides," *CIBA Foundation Symposium 140* :16-31 (1988).
Lee, "High Cell-Density Culture of *Escherichia coli*," *TIBECH 14* :98-105 (1996).
Kobayashi, et al., "Cobalt Proteins," *Eur. J. Biochem. 261* :1-9 (1999).
Kobayashi, et al., "Enzymatic Synthesis of Acrylamide: A Success Story Not Yet Over," *TIBECH 10* :402-408 (1992).
Komeda, et al., "A Novel Transporter Involved in Cobalt Uptake," *Proc. Natl. Acad. Sci. USA 94* :36-41 (1997).
Martinkova, et al., "Synthetic Applications of Nitrile-Converting Enzymes," *Curr. Org. Chem. 7* :1279-1295 (2003).
Nojiri, et al., "Functional Expression of Nitrile Hydratase in *Escherichia coli*: Requirement of a Nitrile Hydratase Activator and Post-Translational Modification of a Ligand Cysteine," *J. Biochem. 125* :696-704 (1999).
Riesenberg, et al., "High-Cell Density Cultivation of Microorganisms," *Appl. Microbiol. Biotechnol. 51* :422-430 (1999).
Wu, et al., "Over-Production of Stereoselective Nitrile Hydratase from *Pseudomonas putida* 5B in *Escherichia coli*: Activity Requires a Novel Downstream Protein," *App. Microbiol. Biotechnol. 48*: 704-708 (1997).
English Language Abstract for Reference B3 above—WO 02/055670.
English Language Abstract for Reference B above—DE 101 55 928.
English Language Abstract for Reference B9 above—JP 5-284982.

* cited by examiner

*Primary Examiner*—Rebecca E. Prouty
*Assistant Examiner*—M. Younus Meah
(74) *Attorney, Agent, or Firm*—Michael A. Sanzo; Law Office of Michael A. Sanzon, LLC

(57) ABSTRACT

The invention relates to a *Rhodococcus* polynucleotide cluster which contains nucleotide sequences which encode polypeptides having the activity of a nitrile hydratase, of an auxiliary protein P15K which activates this enzyme and of a cobalt transporter, to transformed microorganisms in which the nucleotide sequences encoding these proteins are present in increased quantity, and to the use of the transformed microorganisms for preparing amides from nitriles.

14 Claims, 3 Drawing Sheets

RHODOCOCCUS NITRILE HYDRATASE

CROSS REFERENCE TO RELATED APPLICATIONS

The present application claims priority to German Application No. 10 2004 013 824.9 filed on Mar. 20, 2004, which is incorporated in its entirety herein by reference.

FIELD OF THE INVENTION

The invention relates to a *Rhodococcus* polynucleotide cluster which contains nucleotide sequences which encode polypeptides having the activity of a nitrile hydratase, of an auxiliary protein P15K which activates this enzyme, and of a cobalt transporter, to microorganisms which are transformed with this cluster and in which the nucleotide sequences encoding these proteins are present in increased quantity, and to the use of the transformed microorganisms for preparing amides from nitriles.

BACKGROUND OF THE INVENTION

A large number of nitrile hydratases have already been described in the literature (Synthetic applications of nitrile-converting enzymes; Martinkova, Ludmila; Mylerova, Veronika; Current Organic Chemistry (2003), 7(13), 1279-1295). Nitrile hydratases have been used since 1983 for producing acrylamide on a scale of several thousand tons per year. This biocatalytic process has proved to be able to compete with the chemical processes (Enzymic synthesis of acrylamide: a success story not yet over; Kobayashi, Michihiko; Nagasawa, Toru; Yamada, Trends in Biotechnology (1992), 10(11), 402-8).

In addition to the nitrile hydratases which can be used for converting acrylonitrile, nitrile hydratases which are particularly suitable for converting methacrylonitrile (A nitrile hydratase of *Pseudonocardia thermophila* and the genes encoding and manufacture of the enzyme for conversion of nitriles to amides (EP 790310), 3-cyanopyridine (Process for producing amides with *Rhodococcus* nitrile hydratase (WO 2002055670) or 2-hydroxynitriles such as 2-hydroxy-4-methylthiobutyro-nitrile (A nitrile hydratase of *Rhodococcus* and its use in the manufacture of amides (WO 2002070717) and Enzymic conversion of α-hydroxynitriles to the corresponding α-hydroxyamides, acids or acid salts, (WO 9832872) have, for example, also been described. By contrast, no nitrile hydratases which can be used to efficiently convert 2-aminonitriles are thus far known. While the *Rhodococcus* sp. Cr4 nitrile hydratase converts 2-hydroxynitriles, for example, with a high degree of activity, it does not convert a simple 2-aminonitrile such as aminoacetonitrile at all (WO 2002070717).

The enzymic conversion of aminonitriles into the corresponding amides opens up an attractive route for synthesizing amino acids since 2-aminoamides can be hydrolyzed readily (WO 2001060789). This process proceeds under mild conditions and with a very high degree of selectivity and without the formation of byproducts such as salts, as accrue in connection with chemical hydrolysis.

Alternatively, amides can also be converted with alkali metal or alkaline earth metal hydroxides into the corresponding salts of the acids. This approach is particularly preferred when using calcium hydroxide for converting 4-methylthio-α-hydroxybutyramide (MHA-amide), since the calcium salt of MHA can be used directly as a feedstuff additive, as a product form which is an alternative to methionine or MHA.

However, for producing a commodity product such as DL-methionine, it is not sufficient to make available a high-activity biocatalyst. In order to increase the activity, it is necessary to establish a system for expressing the genes which are to be amplified. One possibility which presents itself is heterologous expression, for example, and in particular, in *Escherichia coli, Bacillus, Pseudomonas, Pichia, Sacharomyces* or *Aspergillus*, since these microorganisms exhibit rapid growth, achieve very high cell densities and are available molecular biological tools which permit very high expression levels (Lee S Y (1996) High cell-density culture of *Escherichia coli*. TIBTECH 14:98-105; Riesenberg D, Guthke R (1999) High-cell-density cultivation of microorganisms. Appl Microbiol Biotechnol 51:422-430).

It is known that at least 3 genes have to be coexpressed for nitrile hydratases to be expressed heterologously. In addition to two structural genes, a corresponding auxiliary protein has to be amplified both for iron-dependent and for cobalt-dependent enzymes (Nojiri M. et al., (1999) Functional expression of Nitrile hydratases in *Escherichia coli*: Requirement of a nitrile hydratase activator and a post-translational modification of a ligand cysteine. J Biochem 125: 696-704 and Over-production of stereoselective nitrile hydratase from *Pseudomonas putida* 5B in *Escherichia coli*: activity requires a novel downstream protein, Wu, S.; Fallon, R. D.; Payne, M. S. Applied Microbiology and Biotechnology (1997), 48(6), 704-708).

In addition to these 3 genes, a further gene, which encodes a cobalt transporter, was found, alongside the structural genes and the auxiliary protein gene, in a gene cluster in *Rhodococcus rhodochrous* J1 (A novel transporter involved in cobalt uptake, Komeda, Hidenobu et al., Proceedings of the National Academy of Sciences of the United States of America (1997), 94(1), 36-41). Overexpression in both *Rhodococcus* and in *E. coli* leads to an increased uptake of $Co^{2+}$ ions from the culture medium. In addition, it was shown that, when the cobalt transporter is coexpressed together with the 3 other proteins, it is possible to achieve the same nitrile hydratase activity at a concentration of Co in the medium which is lower than when the structural genes and the auxiliary protein are expressed on their own. However, according to Komeda et al., this effect only occurs in *Rhodococcus* at concentrations of less than 42 µM.

EP 0 362 829 discloses the fermentation of *Rhodococcus rhodochrous* in the presence of cobalt salts.

DESCRIPTION OF THE INVENTION

The object of the invention is to make available nitrile hydratases which possess high activity and which, in particular, convert α-aminonitriles into amides.

The invention relates to the following:
1. Isolated polynucleotide clusters, from *Rhodococcus*, especially from *Rhodococcus opacus* which contain four nucleotide sequences which encode four polypeptides which possess amino acid sequences which are in each case at least 90% identical to the amino acid sequences contained in the sequences SEQ ID NO:2 to SEQ ID NO:5, with the polypeptides possessing the activities of a nitrile hydratase, composed of an α subunit and a β subunit, of the auxiliary protein P15K and of a cobalt transporter.
2. Polynucleotides, selected from the group:
   a) polynucleotide consisting of positions 1 to 708 in the nucleotide sequence SEQ ID NO:1 or in the nucleotide sequence which is complementary thereto, b) polynucleotide possessing a nucleotide sequence which corresponds to the sequence from a) within the bounds of the degeneracy of the genetic code,
c) polynucleotide which hybridizes, under stringent conditions, with the complementary sequences a) or b), and
d) polynucleotide possessing a nucleotide sequence from a), b) or c) which contains functionally neutral sense mutations, with the polynucleotides encoding the β subunit of the nitrile hydratase.

3. Polynucleotides, selected from the group:
a) polynucleotide comprising positions 710 to 1327 in the nucleotide sequence SEQ ID NO:1 or in the nucleotide sequence which is complementary thereto,
b) polynucleotide possessing a nucleotide sequence which corresponds to the sequence from a) within the bounds of the degeneracy of the genetic code,
c) polynucleotide which hybridizes, under stringent conditions, with the complementary sequences a) or b), and
d) polynucleotide possessing a nucleotide sequence from a), b) or c) which contains functionally neutral sense mutations, with the polynucleotides encoding the α subunit of the nitrile hydratase.

4. Polynucleotides, selected from the group:
a) polynucleotide comprising positions 1324 to 1737 in the nucleotide sequence SEQ ID NO:1 or in the nucleotide sequence which is complementary thereto,
b) polynucleotide possessing a nucleotide sequence which corresponds to the sequence from a) within the bounds of the degeneracy of the genetic code,
c) polynucleotide which hybridizes, under stringent conditions, with the complementary sequences a) or b), and
d) polynucleotide possessing a nucleotide sequence from a), b) or c) which contains functionally neutral sense mutations, with the polynucleotides encoding the auxiliary protein P15K.

5. Polynucleotides, selected from the group:
a) polynucleotide comprising positions 2076 to 3146 in the nucleotide sequence SEQ ID NO:1 or in the nucleotide sequence which is complementary thereto,
b) polynucleotide possessing a nucleotide sequence which corresponds to the sequence from a) within the bounds of the degeneracy of the genetic code,
c) polynucleotide which hybridizes, under stringent conditions, with the complementary sequences a) or b), and
d) polynucleotide possessing a nucleotide sequence from a), b) or c) which contains functionally neutral sense mutations, with the polynucleotides encoding a protein which has the activity of a cobalt transporter.

6) Polypeptide according to 2) or 3) which contains the amino acid sequences SEQ ID NO:2 and SEQ ID NO:3, with the polypeptide exhibiting the activity of a nitrile hydratase.

7) Polypeptide according to 4) which contains the amino acid sequence SEQ ID NO:6, with the polypeptide exhibiting the activity of the auxiliary protein P15 K.

8) Polypeptide according to 5) which contains the amino acid sequence SEQ ID NO:5, with the polypeptide exhibiting the activity of a cobalt transporter.

9) Probe or primer, which contains at least 20 consecutive nucleotides within positions 1 to 1327 from the nucleotide sequence SEQ ID NO:1 or its complementary form.

10) Probe or primer, which contains at least 20 consecutive nucleotides within positions 1324 to 1737 from the nucleotide sequence SEQ ID NO:1 or its complementary form.

11) Probe or primer, which contains at least 20 consecutive nucleotides within positions 2076 to 3146 from the nucleotide sequence SEQ ID NO:1 or its complementary form.

12) Isolated polynucleotide according to 2) and 3) which hybridizes, under stringent conditions, with the complement comprising positions 1 to 1327 from SEQ ID NO:1, with the stringent conditions comprising washing in 5×SSC at a temperature of from 50 to 68° C.

13) Isolated polynucleotide according to 4) which hybridizes, under stringent conditions, with the complement comprising positions 1324 to 1737 from SEQ ID NO:1, with the stringent conditions comprising washing in 5×SSC at a temperature of from 50 to 68° C.

14) Isolated polynucleotide according to 5), which hybridizes, under stringent conditions, with the complement comprising positions 2076 to 3146 from SEQ ID NO:1, with the stringent conditions comprising washing in 5×SSC at a temperature of from 50 to 68° C.

15) Vectors which contain (a) polynucleotide(s) selected from 1) to 5) and 12) to 14), or according to 2), 3) and 4) or according to 5).

16) Vector pUD15, comprising the nucleotide sequence SEQ ID No. 24, containing the sequences according to 2), 3), and 6) from SEQ ID NO:1, with the start codon gtg having been changed to atg.

17) Vector pUD16, comprising the nucleotide sequence SEQ ID NO:25, containing the sequence according to 5), with the start codon ttg having been changed to atg.

18) Host cell, which is transformed or transfected by introducing a polynucleotide according to 1) to 5) and 12) to 14). The host cell can be a eukaryote or prokaryote which is known to have an expression system of adequate stability.

19) Host cell, which is transformed by introducing a vector according to 15) to 17).

20) Transformed host cell according to 18) or 19), with the host cell being a bacterium of the family Enterobacteriaceae, in particular *Escherichia*.

Vector DNA can be introduced into eukaryotic or prokaryotic cells using known transformation or transfection techniques.

"Transformation", "transfection", "conjugation" and "transduction" refer to procedures for introducing foreign DNA which are known in the prior art.

The invention also relates to polynucleotides which are essentially composed of a polynucleotide sequence which can be obtained by using hybridization to screen an appropriate *Rhodococcus opacus* gene library which contains the complete gene, or parts thereof, with a probe which contains the sequences of the polynucleotides according to the invention from SEQ ID No:1, or fragments thereof, and isolating said polynucleotide sequence.

Polynucleotides which contain the sequences according to the invention are suitable for use as hybridization probes for RNA, cDNA and DNA, for the purpose of isolating nucleic acids or polynucleotides or full-length genes which encode the proteins according to the invention or for the purpose of isolating nucleic acids or polynucleotides or genes whose sequences exhibit a high degree of similarity with those of the genes according to the invention. They can also be applied, as probes, on what are termed arrays, microarrays or DNA chips for the purpose of detecting and determining the corresponding polynucleotides or sequences, such as RNA or cDNA, which are derived therefrom.

Polynucleotides which contain the sequences according to the invention are also suitable for use as primers which can be used, together with the polymerase chain reaction (PCR), to prepare DNA from genes which encode the proteins according to the invention.

These oligonucleotides, which serve as probes or primers, contain at least 25 or 30, preferably at least 20, very particularly preferably at least 15, consecutive nucleotides. Oligonucleotides having a length of at least 40 or 50 nucleotides are likewise suitable. Where appropriate, oligonucleotides having a length of at least 100, 150, 200, 250 or 300 nucleotides are also suitable.

"Isolated" means taken out of its natural environment.

In general, "polynucleotide" refers to polyribonucleotides and polydeoxyribonucleotides, with it being possible for the RNA or DNA to be unmodified or modified.

The polynucleotides according to the invention encompass polynucleotides as depicted in SEQ ID No. 1, or fragments contained therein, and also polynucleotides which are at least 90%, 93%, 95%, 97% or 99% identical to the polynucleotides as depicted in SEQ ID NO:1 or fragments contained therein.

"Polypeptides" are understood as being peptides or proteins which contain two or more amino acids which are linked by way of peptide bonds.

The polypeptides according to the invention encompass a polypeptide as depicted in the sequences SEQ ID NO:2 to SEQ ID NO:4 and SEQ ID NO:6 and also polypeptides which are at least 90%, and particularly preferably at least 91%, 95%, 97% or 99%, identical to the polypeptides as depicted in the sequences SEQ ID NO:2 to SEQ ID NO: 4 and SEQ ID NO:6.

The SEQ ID NO:1 polynucleotides contain several individual sequences which encode different proteins. The sequences for the α subunit and the auxiliary protein P15K overlap each other.

The genes which encode the α subunit and the β subunit of nitrile hydratase have to be expressed jointly in order to obtain an active protein.

SEQ ID NO:2 depicts the amino acid sequence of the β subunit, and SEQ ID NO:3 depicts that of the α subunit, of the protein which exhibits nitrile hydratase activity.

SEQ ID NO:2 is derived from positions 1 to 708, and SEQ ID NO:3 is derived from positions 710 to 1327, of the nucleotide sequence SEQ ID NO:1.

The amino acid sequence of the auxiliary protein P15K is to be found in SEQ ID NO:6, corresponding to positions 1324 to 1737 in the nucleotide sequence SEQ ID NO:1.

The auxiliary protein activates the nitrile hydratase and has to be present, together with this enzyme, in the microorganism which is forming the nitryl hydratase.

SEQ ID NO:4 stands for the amino acid sequence of the cobalt transporter and is derived from positions 2076 to 3146 of the nucleotide sequence SEQ ID NO:1.

PatentIN Version 3.1 translates the start codon ttg in SEQ ID NO:4 as leucine and translates the start codon gtg in SEQ ID NO:6 as valine. The correct amino acid is methionine.

It has been found that the nitrile hydratase activity in E. coli is increased many times over by coexpressing the cobalt transporter. This is also the case when high concentrations of cobalt are used in the medium, with these concentrations being orders of size above the concentrations which occur naturally. Surprisingly, coexpressing the cobalt transporter does not lead to any poisoning of the organism but only to a slightly increased sensitivity of the cells towards high cobalt concentrations in the medium.

In order to isolate the gene cluster according to the invention, a gene library of this microorganism is generally first of all prepared in Escherichia coli (E. coli). The preparation of gene libraries is described in well-known textbooks and manuals. Examples which may be mentioned are the textbook by Winnacker: Gene und Klone, Eine Einführung in die Gentechnologie [Genes and clones, an introduction to recombinant DNA technology] (Verlag Chemie, Weinheim, Germany, 1990) or the manual by Sambrook et al.: Molecular Cloning, A Laboratory Manual (Cold Spring Harbor Laboratory Press, 1989). A very well known gene library is that of the E. coli K-12 strain W3110, which was prepared by Kohara et al. (Cell 50, 495-508 (1987)) in λ vectors. Bathe et al. (Molecular and General Genetics, 252:255-265, 1996) describe a gene library of C. glutamicum ATCC13032, which was prepared in the E. coli K-12 strain NM554 (Raleigh et al., 1988, Nucleic Acids Research 16:1563-1575) using the cosmid vector SuperCos I (Wahl et al., 1987, Proceedings of the National Academy of Sciences USA, 84:2160-2164).

It is also possible to use plasmids such as pBR322 (Bolivar, Life Sciences, 25, 807-818 (1979)) or pUC9 (Vieira et al., 1982, Gene, 19:259-268) for preparing a gene library in E. coli. Suitable hosts are, in particular, E. coli strains which are restriction defective and recombination defective. An example of these strains is the strain DH5αmcr, which has been described by Grant et al. (Proceedings of the National Academy of Sciences USA, 87 (1990) 4645-4649). The long DNA fragments which have been cloned using cosmids can then in turn be subcloned into common vectors which are suitable for sequencing and then sequenced as described, for example, in Sanger et al. (Proceedings of the National Academy of Sciences of the United States of America, 74:5463-5467, 1977).

The resulting DNA sequences can then be investigated using known algorithms or sequence analysis programs such as that of Staden (Nucleic Acids Research 14, 217-232 (1986)), that of von Marck (Nucleic Acids Research 16, 1829-1836 (1988)) or the GCG program of Butler (Methods of Biochemical Analysis 39, 74-97 (1998)).

Coding DNA sequences which ensue from the sequences contained in from SEQ ID No. 1 as a result of the degeneracy of the genetic code likewise form part of the subject matter of the invention. In the same way, DNA sequences which hybridize with these sequences, or parts thereof, form part of the subject matter of the invention. Furthermore, conservative amino acid substitutions, such as the replacement of glycine with alanine, or of aspartic acid with glutamic acid, in proteins are known in the field as sense mutations which do not lead to any fundamental change in the activity of the protein, i.e. are functionally neutral. It is furthermore known that changes at the N terminus and/or C terminus of a protein may not significantly impair the function of the protein or may even stabilize it. The skilled person can find information in this regard in, inter alia, Ben-Bassat et al. (Journal of Bacteriology 169:751-757 (1987)), O'Regan et al. (Gene 77:237-251 (1989)), Sahin-Toth et al. (Protein Sciences 3:240-247 (1994)), and in Hochuli et al. (Bio/Technology 6:1321-1325 (1988)) and in known textbooks of genetics and molecular biology.

Finally, DNA sequences which are prepared by the polymerase chain reaction (PCR) using primers which ensue from SEQ ID NO: 1 also form part of the subject matter of the invention. These oligonucleotides typically have a length of at least 15 nucleotides.

The skilled person can find instructions for identifying DNA sequences by means of hybridization in, inter alia, the manual "The DIG System Users Guide for Filter Hybridization" published by the company Boehringer Mannheim GmbH (Mannheim, Germany, 1993) and in Liebl et al. (International Journal of Systematic Bacteriology (1991) 41: 255-260). The hybridization takes place under stringent conditions, i.e. the only hybrids to be formed are those in which the probe and target sequence, i.e. the polynucleotides treated with the probe, are at least 90% identical. It is known that the stringency of the hybridization, including the washing steps, is influenced or determined by varying the buffer composition, the temperature and the salt concentration. The hybridization reaction is preferably carried out at a stringency which is relatively low as compared with that of the washing steps (Hybaid Hybridisation Guide, Hybaid Limited, Teddington, UK, 1996).

For example, a 5×SSC buffer can be used, at a temperature of approx. 50° C.-68° C., for the hybridization reaction. Under these conditions, probes can also hybridize with polynucleotides which exhibit less than 70% identity with the sequence of the probe. These hybrids are less stable and are removed by washing under stringent conditions. This can, for example, be achieved by lowering the salt concentration down to 2×SSC and, where appropriate, subsequently to 0.5×SSC (The DIG System User's Guide for Filter Hybridisation, Boehringer Mannheim, Mannheim, Germany, 1995), with the temperature being set at approx. 50° C.-68° C. It is possible, where appropriate, to lower the salt concentration down to 0.1×SSC. By increasing the hybridization temperature stepwise from 50° C. to 68° C. in steps of approx. 1-2° C., it is possible to isolate polynucleotide fragments which possess, for example, at least 90% to 95% identity with the sequence of the probe which is employed. Further hybridization instructions can be obtained on the market in the form of kits (e.g. DIG Easy Hyb supplied by Roche Diagnostics GmbH, Mannheim, Germany, Catalog No. 1603558).

The skilled person can find instructions for amplifying DNA sequences using the polymerase chain reaction (PCR) in, inter alia, the manual by Gait: Oligonucleotide synthesis: A Practical Approach (IRL Press, Oxford, UK, 1984) and in Newton and Graham: PCR (Spektrum Akademischer Verlag, Heidelberg, Germany, 1994).

In general, the approach is to clone a gene which is expressed at a high level into a vector having a low copy number and to clone genes which are expressed more weakly into a vector with a higher copy number and/or a strong promoter. The host cells are transformed with these vectors such that they then in each case contain at least one additional copy, as compared with the starting organism, of the nucleotide sequences which encode the formation of nitrile hydratase or of the other proteins.

It has been found to be advantageous to express the cobalt transporter-encoding gene at a lower level, for example using a vector of low copy number, i.e. at least one copy less, than that for the polynucleotide sequences which encode the α and β subunits and the P15K auxiliary protein. Differential expression of said genes can also be achieved by using promoters of differing strength.

The nucleotides encoding the α and β subunits, on the one hand, and the auxiliary protein, on the other hand, are preferably located jointly on one vector and either share a common promoter or have two separate promoters.

The transformed or recombinant microorganisms which have been prepared in this way likewise form part of the subject matter of the invention.

It has been found that amplifying the genes encoding the nitrile hydratase, the P15K auxiliary protein and the cobalt transporter in microorganisms leads to an increased production of the nitrile hydratase or else to an increased activity of the nitrile hydratase.

In this connection, the term "amplification" describes the increase in the intracellular activity, in a microorganism, of one or more enzymes, which are encoded by the corresponding DNA, which is acheived by, for example, increasing the copy number of the gene or genes, using a strong promoter or using a gene which encodes a corresponding enzyme having a high activity, and, where appropriate, combining these measures.

In order to achieve overexpression, the promoter and regulatory region or the ribosomal binding site, which is located upstream of the structural gene, can be mutated. Expression cassettes which are incorporated upstream of the structural gene act in the same manner. In addition, it is possible, by using inducible promoters, to increase expression during the course of the fermentative amino acid production. Expression is likewise improved by measures taken to extend the lifetime of the mRNA.

In addition, the enzyme activity is also augmented by preventing the enzyme protein from being broken down. The genes or gene constructs can either be present in plasmids having differing copy numbers or be integrated, and amplified, in the chromosome. Alternatively, it is also possible to achieve overexpression of the genes concerned by altering the composition of the medium and the conduct of the culture.

In general, the amplification, in particular overexpression, measures which are taken increase the activity or concentration of the corresponding protein by at least 10%, 25%, 50%, 75%, 100%, 150%, 200%, 300%, 400% or 500%, and maximally up to 1000% or 2000%, based on that of the wild-type protein or on the activity or concentration of the protein in microorganisms which are not transformed with the nucleotide sequences according to the invention.

The invention also relates to the provision of vectors which are in general autonomously replicable in the selected host strains, which are compatible with each other and which contain at least nucleotide sequences as claimed in claims 2, 3 and 4 or a nucleotide sequence as claimed in claim 4.

Vector DNA can be introduced into eukaryotic or prokaryotic cells using known transformation techniques.

The host organisms employed are preferably microorganisms, such as *Pseudomonas*, *Pichia*, various yeasts, *Saccaromyces*, *Aspergillus* or the family *Streptomyces*, in particular *E. coli*, for which expression systems are existing. Microorganisms of the genus *Rhodococcus* are also suitable.

The invention also relates to a process for preparing nitrile hydratase originating from *Rhodococcus*, especially *Rhodococcus opacus* or microorganisms comprising this enzyme, in which a) a transformed microorganism, which comprises overexpressed genes having the nucleotide sequences as claimed in claims 1 to 4, is fermented in the presence of from 0.15 to 4 mM (mmol/l) $Co^{2+}$, in particular from 0.3 to 4 mM, under conditions which lead to the formation of the nitrile hydratase, b) this enzyme is allowed to accumulate in the microorganism, and c) this enzyme is isolated from the cells, or d) the microorganisms are harvested and isolated as resting cells which comprise the enzyme.

The recombinantly produced nitrile hydratase converts α-aminonitriles with an activity of >50 U/mg of dry biomass.

The fermentation is preferably carried out in the presence of from 0.5 to 3.5 mM $Co^{2+}$, in particular of from 0.7 to 3 mM, which is preferably added to the fermentation broth as soluble salt.

The microorganisms which are used in accordance with the invention can be cultured continuously or discontinuously, in a batch process or a fed batch process or a repeated fed batch process. A summary of known culturing methods is given in the textbook by Chmiel (Bioprozeβtechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium which is to be used must suitably satisfy the requirements of the given strains.

Descriptions of media for culturing different microorganisms are to be found in the manual "Manual of Methods for General Bacteriology" published by the American Society for Bacteriology (Washington D.C., USA, 1981).

Carbon sources which can be used are sugars and carbohydrates, such as glucose, sucrose, lactose, fructose, maltose, molasses, starch and cellulose, oils and fats, such as soybean oil, sunflower oil, peanut oil and coconut oil, fatty acids, such as palmitic acid, stearic acid and linoleic acid, alcohols, such as glycerol and ethanol, and organic acids, such as acetic acid. These substances can be used individually or as mixtures.

Nitrogen sources which can be used are nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources can be used individually or as mixtures.

The phosphorus sources used can be phosphoric acid, potassium dihydrogen phosphate or dipotassium hydrogen phosphate or the corresponding sodium-containing salts. The culture medium has furthermore to contain metal salts, such as magnesium sulfate or iron sulfate, which are required for growth. Finally, it is possible to employ essential growth substances, such as amino acids and vitamins, in addition to the abovementioned substances. The abovementioned added substances can be added to the culture in the form of a once-only mixture or fed in, in a suitable manner, during the culture.

Basic compounds, such as sodium hydroxide, potassium hydroxide, ammonia or ammonia water, or acidic compounds, such as phosphoric acid or sulfuric acid, are used, in a suitable manner, for controlling the pH of the culture. Antifoamants, such as fatty acid polyglycol esters, can be used for controlling foam formation. Suitable substances which act selectively, such as antibiotics, can be added to the medium, in order to maintain the stability of plasmids. Oxygen and oxygen-containing gas mixtures, such as air, are passed into the culture in order to maintain aerobic conditions. The temperature of the culture is normally from 10° C. to 40° C. and preferably from 10° C. to 30° C. The culture is preferably continued at least until it has passed through the logarithmic phase of growth. This objective is normally achieved within from 10 hours to 70 hours.

The invention also relates to a process for enzymically preparing amides from nitrites, which comprises the following steps:

a) converting a nitrile group-containing compound using a Rhodococcus, especially Rhodococcus opacus enzyme which exhibits nitrile hydratase activity, and
b) where appropriate, separating off the amide.

In one process variant, the cells are harvested, washed and taken up, as a suspension, in a buffer at a pH of 5-9, in particular of from 6.8 to 7.9. The concentration of the resting cells is generally 1-25%, in particular from 1.5 to 15% (wet weight/v). The cells can be permeabilized using physical or chemical methods, for example toluene as described in Wilms et al., J. Biotechnol., Vol 86 (2001), 19-30, such that the nitrile compounds which are to be transformed can penetrate through the cell wall and the resulting amide can escape.

The biocatalyst (whole-cell catalyst) is outstandingly stable, such that product concentrations of more than 100 g/l can be achieved.

It is also possible to use known methods to separate off the nitrile hydratase according to the invention from the cells and, where appropriate, purify it and use it for converting the nitriles.

The invention also relates to a process which is characterized in that compounds of the general formulae

in which:
X: is OH, H, alkyl having from 1 to 4 C atoms, aryl, or, in particular, $NH_2$;
R: is H, saturated alkyl radical having from 1 to 12 C atoms, branched or unbranched, optionally substituted by NH2, alkenyl radicals having from 1 to 12 C atoms, branched or unbranched, cycloalkyl groups having from 3 to 6 C atoms,
alkylthio group-substituted alkylene radicals, where alkyl in this case corresponds to a $C_1$ to $C_3$ radical and alkylene corresponds to a bivalent $C_3$ to $C_8$ radical,
R': is H, or alkyl having from 1 to 3 C atoms,
R": is a mononuclear or binuclear aromatic ring, which possesses from 6 to 12 C atoms and which is optionally substituted by one or two alkyl groups (C1-C3) or Cl or F.
Alkylnitrile having from 1 to 6 C atoms.

are converted into the corresponding amides.
The following nitrites are preferably converted:
saturated mononitriles:
acetonitrile, propionitrile, butyronitrile, isobutyronitrile, valeronitrile, isovaleronitrile and capronitrile,
saturated dinitriles:
malonitrile, succinonitrile, glutaronitrile and adiponitrile,
aromatic unsubstituted and substituted mononitriles and dinitriles:
benzonitrile, 2,6-difluorobenzonitrile, phthalonitrile, isophthalonitrile and terephthalonitrile,
α-aminonitriles:
α-aminopropionitrile, α-aminomethylthiobutyronitrile, α-aminobutyronitrile, aminoacetonitrile, all nitrites derived from natural amino acids, α-amino-3,3-dimethylpropionitrile and α-amino-2,3-dimethylpropionitrile
nitrites containing carboxyl groups:
cyanoacetic acid
β-aminonitriles:
3-aminopropionitrile unsaturated nitriles:
acrylonitrile, methacrylonitrile, allyl cyanide and crotononitrile α-hydroxynitriles:
α-hydroxy-n-propionitrile, α-hydroxy-n-butyronitrile, α-hydroxyisobutyronitrile, α-hydroxy-n-hexanonitrile, α-hydroxy-n-heptyronitrile, α-hydroxy-n-octanonitrile, α,γ-dihydroxy-β,β-dimethylbutyronitrile, acrolein cyanohydrin, methacrylaldehyde cyanohydrin, 3-chlorolactonitrile, 4-methylthio-α-hydroxybutyronitrile and α-hydroxy-α-phenylpropionyl.

The concentration, in the reaction solution, of the nitrites to be converted is not restricted to specific ranges.

In order to avoid the enzyme activity being inhibited by the substrate, the concentration of the nitrile is in general kept to from 0.001 to 10 w/w %, in particular from 0.1 to 2 w/w %, based on the quantity of the biocatalyst as dried cell mass. All of the substrate can be added at the beginning of the reaction or the substrate can be added continuously or discontinuously during the reaction.

A solubilizer can be added if the solubility of the nitrile compound in the aqueous reaction system is too low.

However, as an alternative, the reaction can also be carried out in a water/organic solvent two-phase system.

When cells of the microorganism are used as enzymically active material, the ratio of the quantity of the cells employed to the substrate quantity is preferably from 0.001 to 8 w/w % as dried cell mass.

The dry weight of the cell mass is determined using an MA45 Moisture Analyser (Sartorius).

It is also possible to use well-known techniques to immobilize the isolated enzyme and then to employ the enzyme in this form.

The reaction is generally carried out at temperatures of from −5° C. to 50° C., in particular of from 0° C. to 30° C., and over a period of from 0.1 to 100 hours.

The pH of the reaction mixture which is to be maintained is not restricted to specific values as long as the enzymic activity is not impaired. After the reaction, the amide which has been formed can, in a known manner, be separated out of the reaction solution and purified.

The invention also relates to a process in which the amide, or the solution containing the amide, is, for example, separated off from the cells of the biomass and the amide is either hydrolyzed to give the corresponding acid or converted into the corresponding salts of the acid in the added presence of alkali metal or alkaline earth metal hydroxides. Preference is given to MHA-amide being hydrolyzed with calcium hydroxide and the corresponding calcium salt being isolated.

EXAMPLES

Example 1

Cloning the *Rhodococcus opacus* Nitrile Hydratase

*Rhodococcus opacus* chromosomal DNA was digested with the restriction enzymes PinAI, PstI and XmaI (Roche) and the fragments were separated on a 0.8% agarose gel. Standard methods (e.g. in Sambrook et al.: Molecular Cloning, A Laboratory Manual, Cold Spring Habor Laboratory Press, 1989) were used to carry out a Southern blot onto a positively charged nylon membrane (Hybond-N+, Amersham). Hybridization was carried out with a DIG-labeled probe in accordance with the manufacturer's (Roche) instructions. The probe was prepared by means of PCR using the degenerate primers 1F and 1R and employing genomic DNA as a template. The primers were derived from homologous regions of the β subunit, with these regions being determined by aligning the sequences of various NHases. Their sequences were obtained from databases. In order to isolate a detected PinAI fragment of approx. 2.2 kb in size, PinAI-cut DNA fragments of between 2 and 2.5 kb were purified by means of preparative gel electrophoresis and ligated into the XmaI-cut vector pUC18 (Promega), and the ligation mixture was transformed into *E. coli* JM109 (Promega). Positive transformants were identified by means of colony hybridization using the same probe. The clones which were obtained in this way contained a 2206 nt insert comprising the gene for the β subunit, and the majority of the gene for the α subunit, of the nitrile hydratase.

In order to obtain the missing sequence, the above-described method, employing the primers 2F and 2R, was used to prepare a new probe which hybridized at the 3' end of the cloned PinAI fragment. The PinAI fragment cloned into pUC18 served as template. Prior to hybridizing with this probe, the color signals, and the first probe, were first of all removed from the above-described membrane in accordance with the manufacturer's (Roche) instructions. A PstI band of approx. 2 kb in size was detected on this membrane using the second probe. As described above, the corresponding DNA fragment was cloned into the vector pUC18, which had been opened with PstI, and the product was transformed into *E. coli* JM109; positive clones were then identified by means of colony hybridization. The PstI fragment is 1883 nt in size and contains a (3') part of the gene for the α subunit of the nitrile hydratase, the gene for the auxiliary protein P15K and a (5') part of the gene for the cobalt transporter.

In order to clone a DNA fragment containing the missing sequence of the cobalt transporter gene, the primers 3F and 3R, and the PstI fragment cloned in pUC18, with this fragment serving as template, were used to prepare a new probe which hybridized at the 3' end of the cloned PstI fragment. This probe was used to detect an XmaI band of approx. 1.7 kb in size on the same membrane, from which color signals and the second probe had in turn been previously removed. The corresponding DNA fragment was cloned into the pUC18 vector, which had been opened with XmaI, and the product was transformed into *E. coli* JM109; positive clones were identified by means of colony hybridization. A probe which had been amplified using the primers 4F and 3R was used for this purpose. The XmaI fragment is 1747 nt in size and contains a (3') part of the gene for the cobalt transporter.

The continuous sequence of the gene cluster, which contains the polynucleotides encoding the α and β subunits of the nitrile hydratase, the auxiliary protein P15K and the cobalt transporter, is depicted in SEQ ID NO:1.

Example 2

Constructing the Expression Vectors

The structural genes were cloned into an expression vector which is known for being used in *E. coli* and in which the inserted genes are under the control of a rhamnose promoter. A second rhamnose promoter was inserted in addition. To achieve this, the gene for the β subunit was amplified using the primers 5F and 5R, which inserted cleavage sites for the restriction enzymes NdeI, BamHI and HindIII. The second rhamnose promoter was amplified using the primers 6F and 6R, which inserted the cleavage sites for the restriction enzymes BamHI, NcoI and HindIII. The gene for the α subunit was amplified using the primers 7F and 7R, which inserted cleavage sites for the restriction enzymes NcoI, KpnI and HindIII. The gene for the P15K protein was amplified using the primers 8F and 8R, which inserted the cleavage sites for the restriction enzymes KpnI and HindIII and altered the start codon from GTG to ATG. The expression vector which was constructed in this way is designated pUD 15.

The restriction map is given in FIG. 1, while the sequence is given in SEQ ID NO:24.

The gene for the cobalt transporter was cloned into another E. coli expression vector in which the inserted genes are also under the control of the rhamnose promoter. For this, the cobalt transporter gene was amplified using the primers 9F and 9R, which inserted the cleavage sites for the restriction enzymes NdeI and HindIII and altered the start codon from TTG to ATG. The expression vector which was constructed in this way is designated pUD 16.

The restriction map is given in FIG. 2, while the sequence is given in SEQ ID NO:25.

The expression plasmids were transformed into the E. coli strain DSM 14459, which is deposited in the Deutschen Sammlung von Mikroorganismen and Zellkulturen [German collection of microorganisms and cell cultures] GmbH (DSMZ).

Primers:

The genes are located on the segments:

| pUD15: | gene for the β subunit: | nt 25-732 |
| | gene for the α subunit: | nt 949-1566 |
| | P15K gene: | nt 1592-2005 |
| pUD16: | gene for the cobalt transporter: | nt 25-1095 |

Example 3

Heterologous Expression of the Nitrile Hydratase in E. coli DSM 14559

DSM 14559 was deposited in connection with DE 101 55 928.

The pUD15-transformed cells were grown, at 37° C. and while shaking, in LB medium (LB broth in accordance with Miller, VWR) which contained 1 mM $CoCl_2$ and 100 µg of ampicillin/ml. The cells transformed with pUD15 and pUD16 were grown in an analogous manner but with the medium additionally containing 50 µg of chloramphenicol/ml. After that, the cells were inoculated over into the same medium 3 times after they had reached an $OD_{600}$ of at least 2. After 12-16 hours, a quantity of the last preliminary culture was inoculated over into a main culture such that this latter had an $OD_{600}$ of 0.1. While the culture medium for the main culture corresponded to that for the preliminary culture, it additionally contained 2 g of L-rhamnose/l. The cells were harvested after 22 hours.

Example 4

Determining the Enzymic Activity

The cells were grown as described in example 3, separated off from the culture medium by centrifugation and resuspended in standard buffer (50 mM potassium phosphate

```
1F  5'-ATG AAY GGH ATY TTC GA-3'

1R  5'-ATC CAG TGY YHG TAG TA-3'

2F  5'-CGA AGA CAT GAT CGT CGT G-3'

2R  5'-ACC GGT CCC ACA CCG A-3'

3F  5'-TCG AGG AGA TCG GAG G-3'

3R  5'-GTA TCG AAG GTG CTC ATC-3'

4F  5'-CGC GGG CTG GGT GAA-3'

5F  5'-CGG CGG AAT TCA AGA AGG AGA CCC GCA TAT GAA CGG-3'

5R  5'-GGT GCA AGC TTGGAT CCT GTC AGA TTC CTC GAG TAG-3'

6F  5'-GCG AAG GAT CCT GCA TGC ATC GAA ATT AAT ACG-3'

6R  5'-CAT CAA GCT TTT CGC CAT GGC TAT ATC TCC TTC-3'

7F  5'-CTG ACA GGA TCC AAG AAG GAG ATA TAG CCA TGG CCG A-3'

7R  5'-GTT GCA AGC TTG GTA CCG CTC AAG ACA TCG CCT CCC T-3'

8F  5'-GTG GGT ACC AAG AAG GAG GCG ATC ATA TGA GCA CGC-3'

8R  5'-GCG GAC GAG TAG CGA AGC TTG TTA GTT CAC CG-3'

9F  5'-TCA AAG CTT GAA GGA GAT ATA CAT ATG ACG ATT ACT-3'

9R  5'-GTC AAG CTT GGT ACC GAC ATC TCA CAC CTT CGA-3'
``` buffer, pH 7.5). 50 µl of this cell suspension were added to 700 µl of the standard buffer and 250 µl of a 200 mM solution of the nitrile in standard buffer were added to start the reaction. In this connection, the concentration of the cells in the cell suspension was gauged such that 5-30% of the nitrile had reacted after 10 min at 20° C. After 10 min at 20° C., the reaction was stopped by adding 20 µl of half-concentrated phosphoric acid and the cells were separated off by centrifugation.

| HPLC analysis | |
| --- | --- |
| Column | Intersil ODS-3V |
| Mobile phase | Mixture composed of 10 mM potassium phosphate buffer, pH 2.3, and acetonitrile in a ratio of 85:15 in the case of methionine nitrile, MHA-nitrile and acetocyanohydrin and of 99:1 in the case of all the other substrates |
| Flow rate | 1 ml/min |
| Detection | UV at 200 nm |

The activity of one unit (U) was defined as the quantity of enzyme which converts 1 µmol of N-formylvaline nitrile to the amide in one minute. The specific activity is given in U per mg of dry biomass (U/mg of DBM).
This is measured using a model MA45 Moisture Analyser (Sartorius).

Example 5

Coexpressing the Genes Encoding the Nitrile Hydratase α Subunit, the β Subunit and the p15K Protein The expression was carried out as described in example 3 using the transformed *E. coli* strain DSM 14459, which harbored plasmid pUD15. The specific activity of the cells was 23 U/mg of DBM.

Example 6

Coexpressing the Genes Encoding the Nitrile Hydratase α Subunit, the β Subunit, the p15K Protein and the Cobalt Transporter The expression was carried out as described in example 3 using the transformed *E. coli* strain DSM 14459 harboring plasmids pUD15 and pUD16. The specific activity of the cells was 81 U/mg of DBM.

Example 7

Substrate Specificity

Various nitriles were converted, in analogy with example 3, using resting transformed *E. coli* DSM 14459 cells which harbored plasmid pUD15. The specific activity which was obtained with N-formylvaline nitrile was set as being equal to 100%. The other activities were given in relation to it. The results are depicted in FIG. 3.

Example 8

Growth of Transformed *E. coli* DSM 14459 in the Presence of Co$^{2+}$ Salts

Transformed *E. coli* DSM 14459 cells, which harbored either only plasmid pUD15 or pUD15 and pUD16, were grown as described in example 3. At the same time, the cobalt concentration in the medium was varied from 0.5 to 2 mM. After 24 hours, the optical densities of the cultures were measured at 600 nm.

| | *E. coli* harboring pUD15 | *E. coli* harboring pUD15 and pUD16 |
| --- | --- | --- |
| 0.5 mM CoC12 | 2.808 | 2.524 |
| 1.0 mM CoC12 | 2.6955 | 2.173 |
| 2.0 mM CoC12 | 2.330 | 2.113 |

It is found that it is only possible to observe a slight influence on the growth of the cells even at high cobalt concentrations.

Example 9

Converting Methionine Nitrile Using Resting Transformed *E. coli* DSM 14459 Cells which Harbor Plasmid pUD15

*E. coli* DSM 14459 cells which harbored plasmid pUD15 were grown, and centrifuged down, as described in example 3. 2.8 g of the cells, based on the wet weight, were resuspended in 47.2 ml of 50 mM potassium phosphate buffer, pH 7.5, and methionine nitrile was added continuously, at 20° C. and while agitating vigorously, at a rate which was such that the concentration did not exceed 15 g/l at any time during the reaction. The pH was maintained constant at 7.5. The reaction was monitored by means of HPLC, as described in example 4. After 320 min, 9.1 g of the nitrile had been completely converted into 10.4 g of amide. This corresponds to a concentration of 176 g/l.

Figure 1:
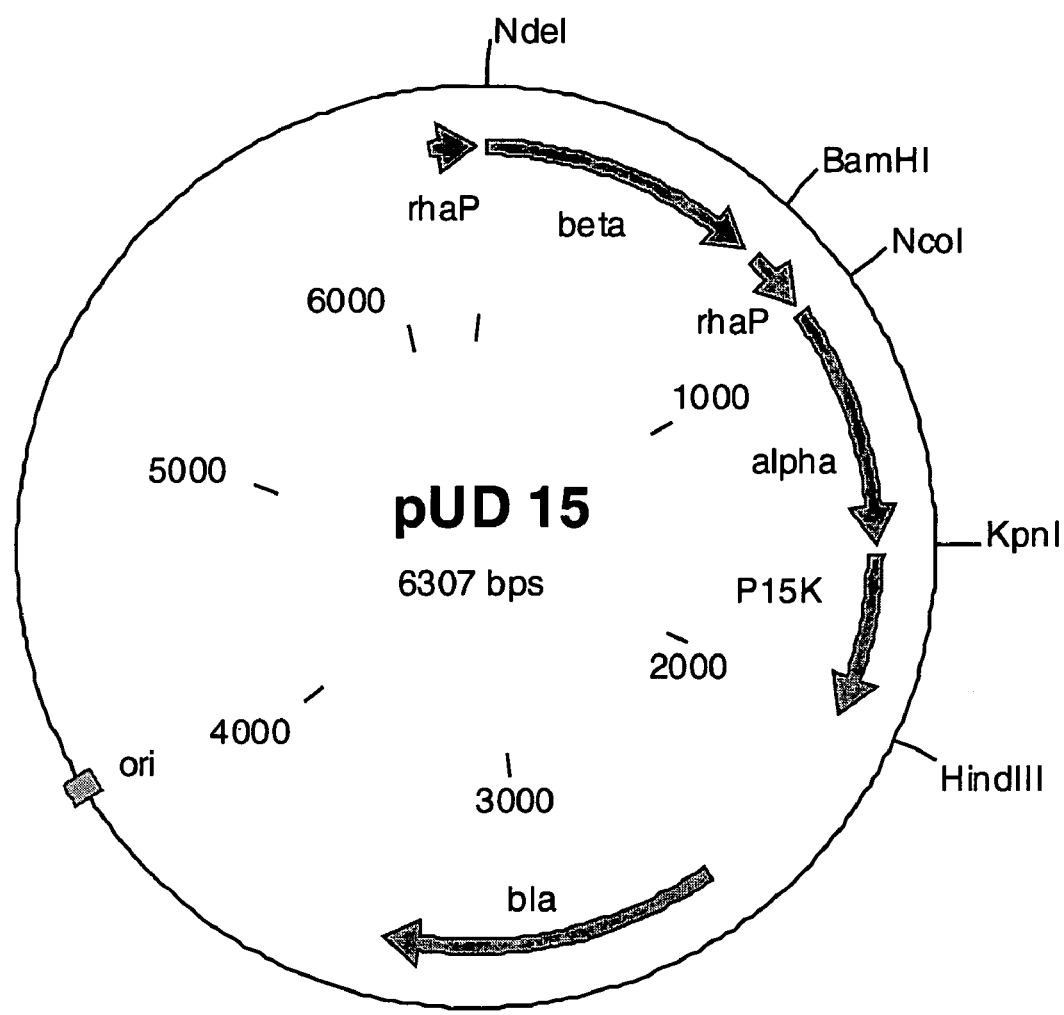
FIG. 1
Figure 2:
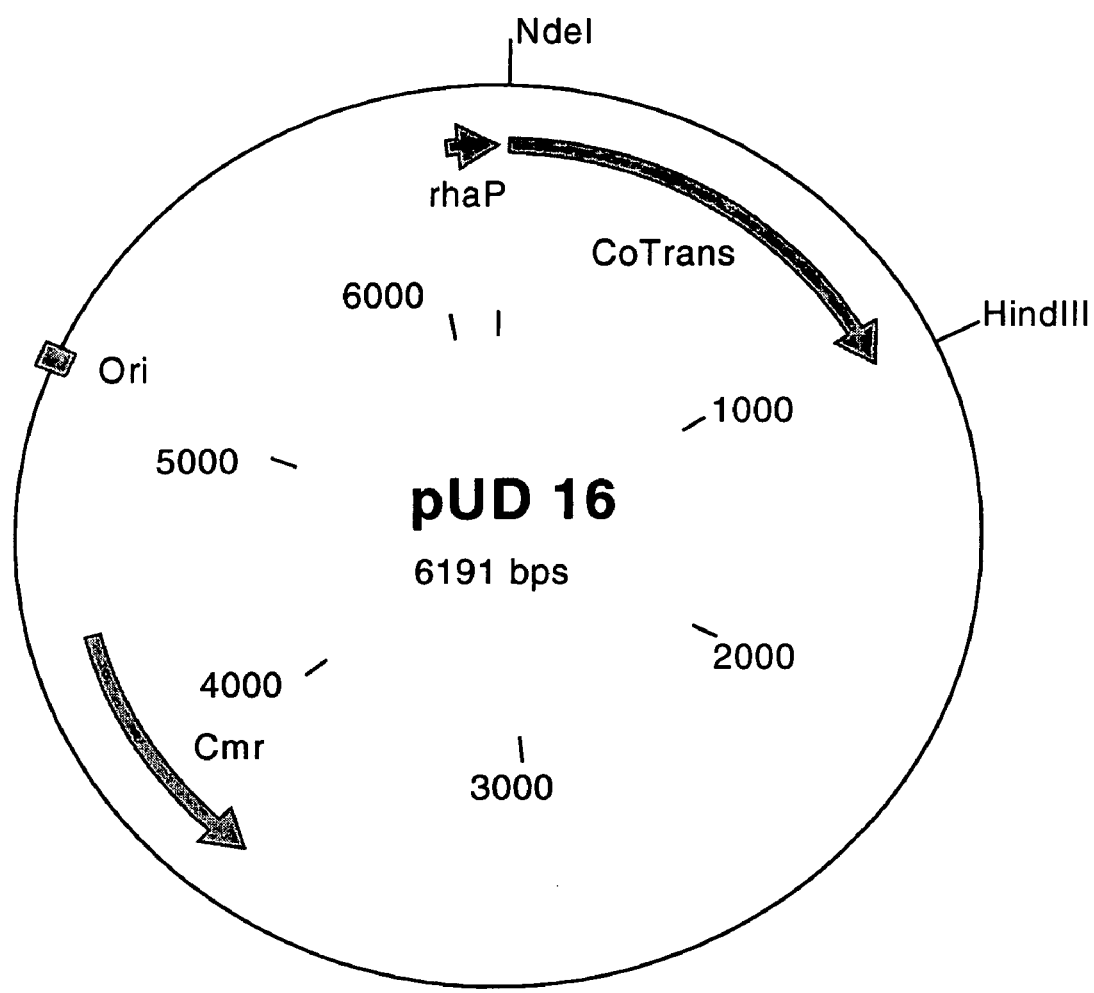
Figure 3:
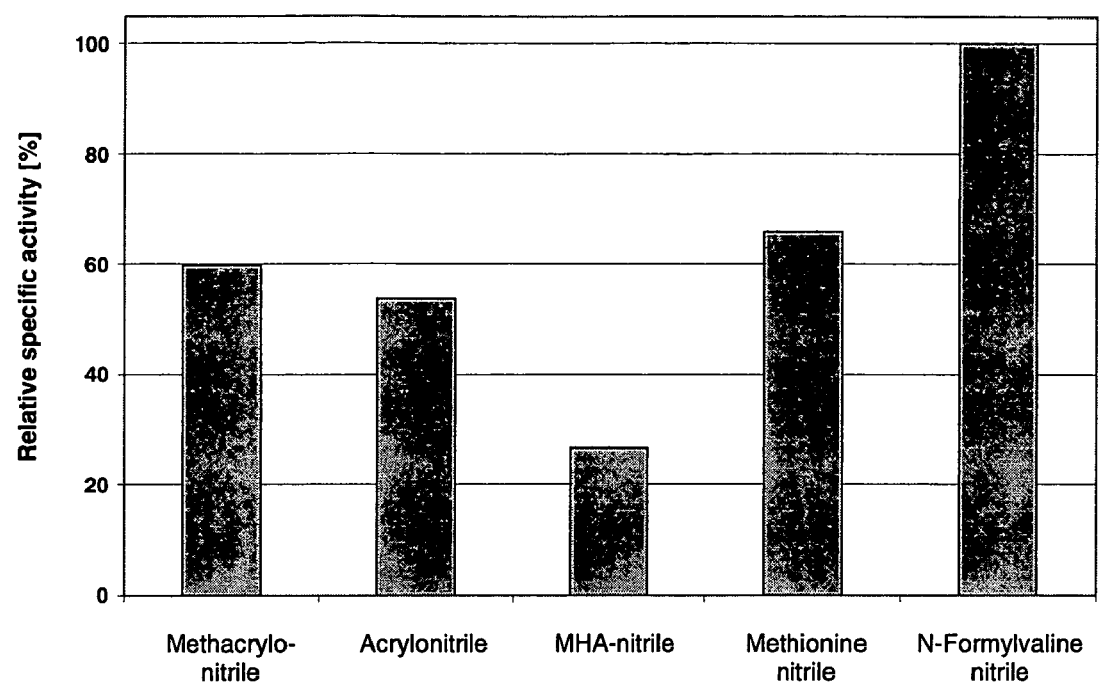

| Plasmid pUD15 | |
| --- | --- |
| rhaP | rhamnose promoter |
| beta | gene for the nitrile hydratase β subunit |
| alpha | gene for the nitrile hydratase α subunit |
| P15K | gene for the auxiliary protein P15K |
| ori | origin of replication |
| bla | gene for resistance to ampicillin (β-lactamase) |

FIG. 2

| Plasmid pUD16 | |
| --- | --- |
| rhaP | rhamnose promoter |
| CoTrans | gene for the cobalt transporter |
| ori | origin of replication |
| Cmr | gene for resistance to chloramphenicol |

FIG. 3

Relative specific activity when converting various nitriles in comparison with the activity when converting N-formylvaline nitrile.

The invention claimed is:

1. An isolated polynucleotide cluster comprising four gene sequences, wherein said gene sequences encode a first polypeptide, a second polypeptide, an auxiliary protein (P15K) and a cobalt transporter protein, and wherein:
   a) said first polypeptide comprises the amino acid sequence of SEQ ID NO:2 and, in the presence of said second polypeptide and auxiliary protein, has nitrile hydratase activity;
   b) said second polypeptide comprises the amino acid of SEQ ID NO:3; and, in the presence of said first polypeptide and auxiliary protein, has nitrile hydratase activity;
   c) said auxiliary protein comprises the amino acid sequence of SEQ ID NO:6, and, in the presence of said first polypeptide and said second polypeptide, has nitrile hydratase activity and
   d) said cobalt transporter protein comprises the amino acid of SEQ ID NO:4, and has cobalt transporter activity.

2. The polynucleotide of claim 1, wherein said polynucleotide comprises a sequence selected from the group consisting of:
   a) a polynucleotide comprising of positions 1 to 708 in the nucleotide sequence SEQ ID NO:1 or a nucleotide sequence which is fully complementary thereto;
   b) a polynucleotide comprising a nucleotide sequence which corresponds to the sequence from a) within the bounds of the degeneracy of the genetic code; and c) a polynucleotide which hybridizes, under stringent conditions with the fully complementary sequences a) or b), wherein said stringent conditions comprise washing in 0.5×SSC at a temperature of 680° C.;

and wherein said sequence encodes the beta subunit of a protein with nitrile hydratase activity.

3. The polynucleotide of claim 1, wherein said polynucleotide comprises a sequence selected from the group consisting of:
   a) a polynucleotide comprising positions 710 to 1327 in the nucleotide sequence SEQ ID NO:1 or in the nucleotide sequence which is fully complementary thereto;
   b) a polynucleotide comprising a nucleotide sequence which corresponds to the sequence from a) within the bounds of the degeneracy of the genetic code; and
   c) a polynucleotide which hybridizes, under stringent conditions, with the fully complementary sequences a) or b) wherein said stringent conditions comprise washing in 0.5×SSC at a temperature of 680° C.;

and wherein said sequence encodes the alpha subunit of a protein with nitrile hydratase activity.

4. The polynucleotide of claim 1, wherein said polynucleotide comprises a sequence selected from the group consisting of:
   a) a polynucleotide comprising positions 1324 to 1737 in the nucleotide sequence SEQ ID NO:1 or in the nucleotide sequence which is fully complementary thereto;
   b) a polynucleotide comprising a nucleotide sequence which corresponds to the sequence from a) within the bounds of the degeneracy of the genetic code; and
   c) a polynucleotide which hybridizes, under stringent conditions, with the fully complementary sequences a) or b) wherein said stringent conditions comprise washing in 0.5×SSC at a temperature of 680° C.;

and wherein said sequence encodes a protein which, in the presence of said first polypeptide and said second polypeptide, has nitrile hydratase activity.

5. The polynucleotide of claim 1, wherein said polynucleotide comprises a sequence selected from the group consisting of:
   a) a polynucleotide comprising positions 2076 to 3146 in the nucleotide sequence SEQ ID NO:1 or in the nucleotide sequence which is fully complementary thereto;
   b) polynucleotide comprising a nucleotide sequence which corresponds to the sequence from a) within the bounds of the degeneracy of the genetic code; and
   c) polynucleotide which hybridizes, under stringent conditions, with the fully complementary sequences a) or b) wherein said stringent conditions comprise washing in 0.5×SSC at a temperature of 680° C.;

and wherein said sequence encodes a protein with the activity of a cobalt transporter protein.

6. A vector comprising a sequence selected from the group consisting of:
   a) the polynucleotide sequence of claim 1;
   b) the polynucleotide sequence of SEQ ID NO:25; and
   c) the polynucleotide sequence of SEQ ID NO:24.

7. An isolated host cell transformed or transfected by introducing the vector of claim 6.

8. The host cell of claim 7, wherein said host cell is of the family Enterobacteriaceae.

9. A process for preparing a nitrile hydratase, comprising:
   a) fermenting a microorganism in which the polynucleotides of paragraphs a)-c) of claim 1 are overexpressed, said fermentation being carried out in the presence of from 0.15 to 4 mM $Co^{2+}$, and under conditions which lead to the formation of the nitrile hydratase; and
   b) allowing said nitrile hydratase to accumulate in said microorganism.

10. The process of claim 9, further comprising:
    c) isolating said nitrile hydratase from the microorganism of step b).

11. The process of claim 9, wherein said microorganism also overexpresses a polynucleotide encoding a cobalt transporter protein, wherein said cobalt transport protein comprises the amino acid of SEQ ID NO:4, and has cobalt transporter activity.

12. The process of claim 11, further comprising:
    c) isolating said nitrile hydratase from the microorganism of step b).

13. The process of claim 9, wherein said microorganism is a host cell comprising a polynucleotide selected from the group consisting of:
    a) a polynucleotide comprising four gene sequences, wherein said gene sequences encode a first polypeptide, a second polypeptide, an auxiliary protein (P15K) and a cobalt transporter protein, and wherein:
       i) said first polypeptide comprises the amino acid sequence of SEQ ID NO:2 and, in the presence of said second polypeptide and auxiliary protein, has nitrile hydratase activity;
       ii) said second polypeptide comprises the amino acid of SEQ ID NO:3; and, in the presence of said first polypeptide and auxiliary protein, has nitrile hydratase activity;
       iii) said auxiliary protein comprises the amino acid sequence of SEQ ID NO:6, and, in the presence of said first polypeptide and said second polypeptide, has nitrile hydratase activity;
       iv) said cobalt transporter protein comprises the amino acid of SEQ ID NO:4, and has cobalt transporter activity;
    b) the nucleotide sequence of SEQ ID NO:25; and
    c) the nucleotide sequence of SEQ ID NO:24.

14. The process of claim 13, wherein said nitrile hydratase converts α-aminonitriles with a specific activity of >50 U/mg of dry biomass.

* * * * *

SEQUENCE LISTING

<160> NUMBER OF SEQ ID NOS: 25

<210> SEQ ID NO 1
<211> LENGTH: 3146
<212> TYPE: DNA
<213> ORGANISM: Rhodococcus opacus
<220> FEATURE:
<221> NAME/KEY: CDS
<222> LOCATION: (1)..(708)
<223> OTHER INFORMATION:
<220> FEATURE:
<221> NAME/KEY: CDS
<222> LOCATION: (710)..(1327)
<223> OTHER INFORMATION:
<220> FEATURE:
<221> NAME/KEY: CDS
<222> LOCATION: (2076)..(3146)
<223> OTHER INFORMATION:

<400> SEQUENCE: 1

```
atg aac ggc atc ttc gat cta ggc gga acc gac ggc atg ggg ccg gtc        48
Met Asn Gly Ile Phe Asp Leu Gly Gly Thr Asp Gly Met Gly Pro Val
1               5                   10                  15 gac aac gac aaa ggc acc gag ccg gtg ttc cgc tca gcg tgg gaa aag        96
Asp Asn Asp Lys Gly Thr Glu Pro Val Phe Arg Ser Ala Trp Glu Lys
            20                  25                  30 gcc gcc ttc tcg atg ttc gca caa ggc gcc cga gct ggc ctc tac aac       144
Ala Ala Phe Ser Met Phe Ala Gln Gly Ala Arg Ala Gly Leu Tyr Asn
        35                  40                  45 atc gac gag ttc cgg cac tgc gtc gag cag atg gac ccc gcc gag tat       192
Ile Asp Glu Phe Arg His Cys Val Glu Gln Met Asp Pro Ala Glu Tyr
    50                  55                  60 tta cta tcg aac tac tac gag cac tgg acg cat gcc gtc gaa cac ttc       240
Leu Leu Ser Asn Tyr Tyr Glu His Trp Thr His Ala Val Glu His Phe
65                  70                  75                  80 gcc cag caa aag aac ctc atc aca gcg gca gag ctc gaa aag cgc acg       288
Ala Gln Gln Lys Asn Leu Ile Thr Ala Ala Glu Leu Glu Lys Arg Thr
                85                  90                  95 cat ttc tac cgg gat aac cca gaa gcc ccc ctt ccg gag cgc aag gac       336
His Phe Tyr Arg Asp Asn Pro Glu Ala Pro Leu Pro Glu Arg Lys Asp
            100                 105                 110 cca gag ctc ctc gac ttc gtg aac acc gcg atc gcg aac ggt ttc gcg       384
Pro Glu Leu Leu Asp Phe Val Asn Thr Ala Ile Ala Asn Gly Phe Ala
        115                 120                 125 gcc tcc cgt gaa acc aat agg tcg gca gca ttc acc atc ggc gac cag       432
Ala Ser Arg Glu Thr Asn Arg Ser Ala Ala Phe Thr Ile Gly Asp Gln
    130                 135                 140 gta ctg att gct gcg gac agt cca ttc gga cac acc cga cgg gcc ggc       480
Val Leu Ile Ala Ala Asp Ser Pro Phe Gly His Thr Arg Arg Ala Gly
145                 150                 155                 160 tac atc cgc ggt aag acc gga gtc atc acc gcg aca cac ggc gcc tac       528
Tyr Ile Arg Gly Lys Thr Gly Val Ile Thr Ala Thr His Gly Ala Tyr
                165                 170                 175 gtc tat ccc gac acc gcc ggt aac ggg ctc ggt gag tgc cca gag cac       576
Val Tyr Pro Asp Thr Ala Gly Asn Gly Leu Gly Glu Cys Pro Glu His
            180                 185                 190 gtc tac acc gtg aag ttc acc gcc acc gaa ctt tgg ggc gaa cag agc       624
Val Tyr Thr Val Lys Phe Thr Ala Thr Glu Leu Trp Gly Glu Gln Ser
        195                 200                 205 ggt gat cgc cac agc acc gtc tat ttc gat gtc tgg gaa ccg tac ctc       672
Gly Asp Arg His Ser Thr Val Tyr Phe Asp Val Trp Glu Pro Tyr Leu
    210                 215                 220
```

-continued

| | | |
|---|---|---|
| tcg ctc gct acc gca ccc tct act cga gga atc tga c atg gcc gaa cag<br>Ser Leu Ala Thr Ala Pro Ser Thr Arg Gly Ile     Met Ala Glu Gln<br>225                 230                 235 | 721 |
| cgc acc gac acc caa ttg cgt aca cac gaa gaa gtc gtc gcc cga gtc<br>Arg Thr Asp Thr Gln Leu Arg Thr His Glu Glu Val Val Ala Arg Val<br>240                 245                 250                 255 | 769 |
| aag gcg ctc gag gcg ctg ctg atc gag aaa ggc gtc atg acg acc gag<br>Lys Ala Leu Glu Ala Leu Leu Ile Glu Lys Gly Val Met Thr Thr Glu<br>                260                 265                 270 | 817 |
| gcc gtc gac cgg atg gcc gag gta tac gag aac gaa gtc ggc ccc cag<br>Ala Val Asp Arg Met Ala Glu Val Tyr Glu Asn Glu Val Gly Pro Gln<br>275                 280                 285 | 865 |
| atc ggc gct cag att gtc gcc aag gcg tgg acc gac ccg aag ttc aag<br>Ile Gly Ala Gln Ile Val Ala Lys Ala Trp Thr Asp Pro Lys Phe Lys<br>                290                 295                 300 | 913 |
| aag agg ttg ctg gcc aat gcc acg act gcc tgc gca gag atg ggc tac<br>Lys Arg Leu Leu Ala Asn Ala Thr Thr Ala Cys Ala Glu Met Gly Tyr<br>305                 310                 315 | 961 |
| ggc ggt ctg cag ggc gaa gac atg atc gtc gtg gaa aac acc gac acc<br>Gly Gly Leu Gln Gly Glu Asp Met Ile Val Val Glu Asn Thr Asp Thr<br>320                 325                 330                 335 | 1009 |
| gta cac aac gcg att gtg tgc acc ctc tgc tcc tgc tac ccg tgg ccg<br>Val His Asn Ala Ile Val Cys Thr Leu Cys Ser Cys Tyr Pro Trp Pro<br>                340                 345                 350 | 1057 |
| gtc ttg ggc ctg cca ccg aac tgg tac aag gca ccg gct tac cgc gca<br>Val Leu Gly Leu Pro Pro Asn Trp Tyr Lys Ala Pro Ala Tyr Arg Ala<br>355                 360                 365 | 1105 |
| cgg atc gtg cgc gaa ccg cgg aag gtc ctc gcc gag gac ttc gac ttt<br>Arg Ile Val Arg Glu Pro Arg Lys Val Leu Ala Glu Asp Phe Asp Phe<br>                370                 375                 380 | 1153 |
| ccc atc ccc gac gac gtc gag atc cgc gtg tgg gac tcg agc gcc gag<br>Pro Ile Pro Asp Asp Val Glu Ile Arg Val Trp Asp Ser Ser Ala Glu<br>385                 390                 395 | 1201 |
| ctg cgc tat tgg gtt tta ccg cag cgc cct gca cac acc gaa aga ttg<br>Leu Arg Tyr Trp Val Leu Pro Gln Arg Pro Ala His Thr Glu Arg Leu<br>400                 405                 410                 415 | 1249 |
| acg gaa tcc gag ctg gta gcg ctg gtc acc cgc gac tcg atg atc ggt<br>Thr Glu Ser Glu Leu Val Ala Leu Val Thr Arg Asp Ser Met Ile Gly<br>                420                 425                 430 | 1297 |
| gtg gga ccg gtg agg gag gcg atg tcg tga gcacgcgcat tgacgcaacc<br>Val Gly Pro Val Arg Glu Ala Met Ser<br>435                 440 | 1347 |
| gagctcgggg aagcacgccg gcgaatcgag gcgttggtgt gtgatctgcc cggtggtgac | 1407 |
| gtaggctcac gcgccttcaa cgagccgtgg gaattgcgtg ccttcgcgat ggccgttgcc | 1467 |
| gtgtatcacc agggtcacta cgaatggagt gagtttcagc tctccctgat cgcgtcgatc | 1527 |
| cgccactggg agcagggcga gggaagggag ccgtggagct actacgagca ctggctcaat | 1587 |
| gcgctcgagt cggtactcgc cgccagcggc gccttatcgg acgcagtggg cctcgatgag | 1647 |
| cgcacgcgcg aagttctcac caccccacgg aacacgaacc accaccatgc acatcgcgaa | 1707 |
| cccgtcgcga tctcatctgc ggtgaactaa cccgcggcgc tactcgtccg ctggccagct | 1767 |
| ctctgcctgc tgtccagcga acgacacctc cgtgacagct tctcgttcac cgacccgatc | 1827 |
| actgattccc gacgcggtta ccaacgagca cccgcgtata acagaaccg caaaggtatc | 1887 |
| gcagctgtcg gggacgagcg aatagcggat cgctcgcggg ggccggaccc atgcagctga | 1947 |
| tgctgctttc gcccgaatag cccagatatc cactggacga ggtgcgaggc ccgatacaag | 2007 |

-continued

```
gcgagcgtca gcaaccggca aaccacagcg tccagagcca gcaccgtcat gtctagaaga    2067 ggaaagca ttg acg att act acc act tcg cca agg cag atc gcc ggt cgg    2117
         Leu Thr Ile Thr Thr Thr Ser Pro Arg Gln Ile Ala Gly Arg
                         445                 450 tgg aca cgt gcc gag cgg caa cga ctg agc gct atc atc ggc acc atc    2165
Trp Thr Arg Ala Glu Arg Gln Arg Leu Ser Ala Ile Ile Gly Thr Ile
455             460                 465                 470 gca ttg ctg cac gtg cta ggt atc gca atg tat ctc ggg cgc tcg ggt    2213
Ala Leu Leu His Val Leu Gly Ile Ala Met Tyr Leu Gly Arg Ser Gly
                475                 480                 485 aac ccg gcc gcc gct ggt agc ctg gct ggc tcg gga ctg ctc gcc tat    2261
Asn Pro Ala Ala Ala Gly Ser Leu Ala Gly Ser Gly Leu Leu Ala Tyr
        490                 495                 500 gtc ctg ggt gcg cgg cac gcg ttc gat gcc gac cac atc gcg gcc atc    2309
Val Leu Gly Ala Arg His Ala Phe Asp Ala Asp His Ile Ala Ala Ile
            505                 510                 515 gac gac acc acc cgc atc atg ctc ctt cgc gga cgc gac ccc gtc ggc    2357
Asp Asp Thr Thr Arg Ile Met Leu Leu Arg Gly Arg Arg Pro Val Gly
520                 525                 530 gtc gga ttc ttt ttc gcc atg ggg cat tcg act gtc gtc ctc gtt ctc    2405
Val Gly Phe Phe Phe Ala Met Gly His Ser Thr Val Val Leu Val Leu
535                 540                 545                 550 tct ctg atc gtc gct ttc gga gcg ggc tcg ctc agt tcg atg gaa gcg    2453
Ser Leu Ile Val Ala Phe Gly Ala Gly Ser Leu Ser Ser Met Glu Ala
                555                 560                 565 tcc cgg gtc gag gag atc gga ggt tac gtc gcg acc tgc gtg gca gtg    2501
Ser Arg Val Glu Glu Ile Gly Gly Tyr Val Ala Thr Cys Val Ala Val
        570                 575                 580 ctg ttc ttg gtg ctg gtg gcc gca ctc aac agt ttc gtt ctg cgc aag    2549
Leu Phe Leu Val Leu Val Ala Ala Leu Asn Ser Phe Val Leu Arg Lys
            585                 590                 595 ctc ctc gct ctg tct cgt cgg atg cgc act ggg gaa gat atc tcc ggc    2597
Leu Leu Ala Leu Ser Arg Arg Met Arg Thr Gly Glu Asp Ile Ser Gly
600                 605                 610 gac ctc gag cgc ggg ctg ggt gaa cgg gga ttg ctc agc tgg ctt ctc    2645
Asp Leu Glu Arg Gly Leu Gly Glu Arg Gly Leu Leu Ser Trp Leu Leu
615                 620                 625                 630 agc ggc cga ttg cgc ggg ctg att cgt tcg tcc tgg cac atg tac ccg    2693
Ser Gly Arg Leu Arg Gly Leu Ile Arg Ser Ser Trp His Met Tyr Pro
                635                 640                 645 gtg ggc ctg ctc atg ggt ctc ggc ctg gaa acc gca tcc gaa gtg aca    2741
Val Gly Leu Leu Met Gly Leu Gly Leu Glu Thr Ala Ser Glu Val Thr
        650                 655                 660 ttg ctg tct ctc act gcc tcc gca gcg agc gga ggt cag cta tcg cta    2789
Leu Leu Ser Leu Thr Ala Ser Ala Ala Ser Gly Gly Gln Leu Ser Leu
            665                 670                 675 atg gcg att gtg agc ctt cca ttg ttg ttt gcc gcg ggg atg agc acc    2837
Met Ala Ile Val Ser Leu Pro Leu Leu Phe Ala Ala Gly Met Ser Thr
680                 685                 690 ttc gat act gca gac tca ctc gtc atg acc cgc gcc tat tcg tgg tcc    2885
Phe Asp Thr Ala Asp Ser Leu Val Met Thr Arg Ala Tyr Ser Trp Ser
695                 700                 705                 710 tat aac gat gcc cag cgc cgc ctt cgc ttc aac act gta acc acg ggt    2933
Tyr Asn Asp Ala Gln Arg Arg Leu Arg Phe Asn Thr Val Thr Thr Gly
                715                 720                 725 gcg acc atg gtc atc ggg ttc ttc gtc gcg gga atc tac gtt tct gga    2981
Ala Thr Met Val Ile Gly Phe Phe Val Ala Gly Ile Tyr Val Ser Gly
        730                 735                 740 ctg ctt gcg ccg cta cca ggg ttc ggt tgg ctg acc cct ctg ggc gcg    3029
Leu Leu Ala Pro Leu Pro Gly Phe Gly Trp Leu Thr Pro Leu Gly Ala
```

-continued

```
Leu Leu Ala Pro Leu Pro Gly Phe Gly Trp Leu Thr Pro Leu Gly Ala
        745                 750                 755 atc gcc gac aac ttc gag ttc ctc ggc tac gca gtc gcc gga ttg ttc      3077
Ile Ala Asp Asn Phe Glu Phe Leu Gly Tyr Ala Val Ala Gly Leu Phe
        760                 765                 770 gtt gct acc tgg gca atc gca gca ctg gtt agc cgg cct cga cgg ctt      3125
Val Ala Thr Trp Ala Ile Ala Ala Leu Val Ser Arg Pro Arg Arg Leu
775                 780                 785                 790 gtc ggc agc tcg aag gtg tga                                           3146
Val Gly Ser Ser Lys Val
                795
```

<210> SEQ ID NO 2
<211> LENGTH: 235
<212> TYPE: PRT
<213> ORGANISM: Rhodococcus opacus

<400> SEQUENCE: 2

```
Met Asn Gly Ile Phe Asp Leu Gly Gly Thr Asp Gly Met Gly Pro Val
1               5                   10                  15

Asp Asn Asp Lys Gly Thr Glu Pro Val Phe Arg Ser Ala Trp Glu Lys
            20                  25                  30

Ala Ala Phe Ser Met Phe Ala Gln Gly Ala Arg Ala Gly Leu Tyr Asn
        35                  40                  45

Ile Asp Glu Phe Arg His Cys Val Glu Gln Met Asp Pro Ala Glu Tyr
    50                  55                  60

Leu Leu Ser Asn Tyr Tyr Glu His Trp Thr His Ala Val Glu His Phe
65                  70                  75                  80

Ala Gln Gln Lys Asn Leu Ile Thr Ala Ala Glu Leu Glu Lys Arg Thr
                85                  90                  95

His Phe Tyr Arg Asp Asn Pro Glu Ala Pro Leu Pro Glu Arg Lys Asp
            100                 105                 110

Pro Glu Leu Leu Asp Phe Val Asn Thr Ala Ile Ala Asn Gly Phe Ala
        115                 120                 125

Ala Ser Arg Glu Thr Asn Arg Ser Ala Ala Phe Thr Ile Gly Asp Gln
    130                 135                 140

Val Leu Ile Ala Ala Asp Ser Pro Phe Gly His Thr Arg Arg Ala Gly
145                 150                 155                 160

Tyr Ile Arg Gly Lys Thr Gly Val Ile Thr Ala Thr His Gly Ala Tyr
                165                 170                 175

Val Tyr Pro Asp Thr Ala Gly Asn Gly Leu Gly Glu Cys Pro Glu His
            180                 185                 190

Val Tyr Thr Val Lys Phe Thr Ala Thr Glu Leu Trp Gly Glu Gln Ser
        195                 200                 205

Gly Asp Arg His Ser Thr Val Tyr Phe Asp Val Trp Glu Pro Tyr Leu
    210                 215                 220

Ser Leu Ala Thr Ala Pro Ser Thr Arg Gly Ile
225                 230                 235
```

<210> SEQ ID NO 3
<211> LENGTH: 205
<212> TYPE: PRT
<213> ORGANISM: Rhodococcus opacus

<400> SEQUENCE: 3

```
Met Ala Glu Gln Arg Thr Asp Thr Gln Leu Arg Thr His Glu Glu Val
1               5                   10                  15
```

```
Val Ala Arg Val Lys Ala Leu Glu Ala Leu Ile Glu Lys Gly Val
            20                  25                  30

Met Thr Thr Glu Ala Val Asp Arg Met Ala Glu Val Tyr Glu Asn Glu
        35                  40                  45

Val Gly Pro Gln Ile Gly Ala Gln Ile Val Ala Lys Ala Trp Thr Asp
 50                  55                  60

Pro Lys Phe Lys Lys Arg Leu Leu Ala Asn Ala Thr Thr Ala Cys Ala
 65                  70                  75                  80

Glu Met Gly Tyr Gly Gly Leu Gln Gly Glu Asp Met Ile Val Val Glu
                85                  90                  95

Asn Thr Asp Thr Val His Asn Ala Ile Val Cys Thr Leu Cys Ser Cys
            100                 105                 110

Tyr Pro Trp Pro Val Leu Gly Leu Pro Pro Asn Trp Tyr Lys Ala Pro
        115                 120                 125

Ala Tyr Arg Ala Arg Ile Val Arg Glu Pro Arg Lys Val Leu Ala Glu
130                 135                 140

Asp Phe Asp Phe Pro Ile Pro Asp Asp Val Glu Ile Arg Val Trp Asp
145                 150                 155                 160

Ser Ser Ala Glu Leu Arg Tyr Trp Val Leu Pro Gln Arg Pro Ala His
                165                 170                 175

Thr Glu Arg Leu Thr Glu Ser Glu Leu Val Ala Leu Val Thr Arg Asp
            180                 185                 190

Ser Met Ile Gly Val Gly Pro Val Arg Glu Ala Met Ser
            195                 200                 205

<210> SEQ ID NO 4
<211> LENGTH: 356
<212> TYPE: PRT
<213> ORGANISM: Rhodococcus opacus

<400> SEQUENCE: 4

Leu Thr Ile Thr Thr Thr Ser Pro Arg Gln Ile Ala Gly Arg Trp Thr
 1               5                  10                  15

Arg Ala Glu Arg Gln Arg Leu Ser Ala Ile Ile Gly Thr Ile Ala Leu
            20                  25                  30

Leu His Val Leu Gly Ile Ala Met Tyr Leu Gly Arg Ser Gly Asn Pro
        35                  40                  45

Ala Ala Ala Gly Ser Leu Ala Gly Ser Gly Leu Leu Ala Tyr Val Leu
 50                  55                  60

Gly Ala Arg His Ala Phe Asp Ala Asp His Ile Ala Ala Ile Asp Asp
65                  70                  75                  80

Thr Thr Arg Ile Met Leu Leu Arg Gly Arg Arg Pro Val Gly Val Gly
                85                  90                  95

Phe Phe Phe Ala Met Gly His Ser Thr Val Val Leu Val Leu Ser Leu
            100                 105                 110

Ile Val Ala Phe Gly Ala Gly Ser Leu Ser Ser Met Glu Ala Ser Arg
        115                 120                 125

Val Glu Glu Ile Gly Gly Tyr Val Ala Thr Cys Val Ala Val Leu Phe
130                 135                 140

Leu Val Leu Val Ala Ala Leu Asn Ser Phe Val Leu Arg Lys Leu Leu
145                 150                 155                 160

Ala Leu Ser Arg Arg Met Arg Thr Gly Glu Asp Ile Ser Gly Asp Leu
                165                 170                 175

Glu Arg Gly Leu Gly Glu Arg Gly Leu Leu Ser Trp Leu Leu Ser Gly
            180                 185                 190
```

```
Arg Leu Arg Gly Leu Ile Arg Ser Ser Trp His Met Tyr Pro Val Gly
            195                 200                 205
Leu Leu Met Gly Leu Gly Leu Glu Thr Ala Ser Glu Val Thr Leu Leu
            210                 215                 220
Ser Leu Thr Ala Ser Ala Ala Ser Gly Gly Gln Leu Ser Leu Met Ala
225                 230                 235                 240
Ile Val Ser Leu Pro Leu Leu Phe Ala Ala Gly Met Ser Thr Phe Asp
                245                 250                 255
Thr Ala Asp Ser Leu Val Met Thr Arg Ala Tyr Ser Trp Ser Tyr Asn
            260                 265                 270
Asp Ala Gln Arg Arg Leu Arg Phe Asn Thr Val Thr Thr Gly Ala Thr
            275                 280                 285
Met Val Ile Gly Phe Phe Val Ala Gly Ile Tyr Val Ser Gly Leu Leu
            290                 295                 300
Ala Pro Leu Pro Gly Phe Gly Trp Leu Thr Pro Leu Gly Ala Ile Ala
305                 310                 315                 320
Asp Asn Phe Glu Phe Leu Gly Tyr Ala Val Ala Gly Leu Phe Val Ala
                325                 330                 335
Thr Trp Ala Ile Ala Ala Leu Val Ser Arg Pro Arg Arg Leu Val Gly
            340                 345                 350
Ser Ser Lys Val
            355

<210> SEQ ID NO 5
<211> LENGTH: 3146
<212> TYPE: DNA
<213> ORGANISM: Rhodococcus opacus
<220> FEATURE:
<221> NAME/KEY: CDS
<222> LOCATION: (1324)..(1737)
<223> OTHER INFORMATION:

<400> SEQUENCE: 5
atgaacggca tcttcgatct aggcggaacc gacggcatgg ggccggtcga caacgacaaa      60
ggcaccgagc cggtgttccg ctcagcgtgg gaaaaggccg ccttctcgat gttcgcacaa     120
ggcgcccgag ctggcctcta caacatcgac gagttccggc actgcgtcga gcagatggac     180
cccgccgagt atttactatc gaactactac gagcactgga cgcatgccgt cgaacacttc     240
gcccagcaaa agaacctcat cacagcggca gagctcgaaa gcgcacgca tttctaccgg     300 gataacccag aagcccccct tccggagcgc aaggaccccag agctcctcga cttcgtgaac     360
accgcgatcg cgaacggttt cgcggcctcc cgtgaaacca ataggtcggc agcattcacc     420
atcggcgacc aggtactgat tgctgcggac agtccattcg acacacccg acgggccggc     480 tacatccgcg gtaagaccgg agtcatcacc gcgacacacg gcgcctacgt ctatcccgac     540
accgccggta acgggctcgg tgagtgccca gagcacgtct acaccgtgaa gttcaccgcc     600
accgaacttt ggggcgaaca gagcggtgat cgccacagca ccgtctattt cgatgtctgg     660
gaaccgtacc tctcgctcgc taccgcaccc tctactcgag aatctgaca tggccgaaca     720 gcgcaccgac acccaattgc gtacacacga agaagtcgtc gcccgagtca aggcgctcga     780
ggcgctgctg atcgagaaag gcgtcatgac gaccgaggcc gtcgaccgga tggccgaggt     840
atacgagaac gaagtcggcc ccagatcgg cgctcagatt gtcgccaagg cgtggaccga     900
cccgaagttc aagaagaggt tgctggccaa tgccacgact gcctgcgcag agatgggcta     960
cggcggtctg cagggcgaag acatgatcgt cgtggaaaac accgacaccg tacacaacgc    1020
```

```
gattgtgtgc accctctgct cctgctaccc gtggccggtc ttgggcctgc caccgaactg    1080
gtacaaggca ccggcttacc gcgcacggat cgtgcgcgaa ccgcggaagg tcctcgccga    1140
ggacttcgac tttcccatcc ccgacgacgt cgagatccgc gtgtgggact cgagcgccga    1200
gctgcgctat tgggttttac cgcagcgccc tgcacacacc gaaagattga cggaatccga    1260
gctggtagcg ctggtcaccc cgactcgat gatcggtgtg ggaccggtga gggaggcgat    1320
```

```
gtc gtg agc acg cgc att gac gca acc gag ctc ggg gaa gca cgc cgg    1368
Val Ser Thr Arg Ile Asp Ala Thr Glu Leu Gly Glu Ala Arg Arg
 1               5                  10                  15 cga atc gag gcg ttg gtg tgt gat ctg ccc ggt ggt gac gta ggc tca    1416
Arg Ile Glu Ala Leu Val Cys Asp Leu Pro Gly Gly Asp Val Gly Ser
         20                  25                  30 cgc gcc ttc aac gag ccg tgg gaa ttg cgt gcc ttc gcg atg gcc gtt    1464
Arg Ala Phe Asn Glu Pro Trp Glu Leu Arg Ala Phe Ala Met Ala Val
     35                  40                  45 gcc gtg tat cac cag ggt cac tac gaa tgg agt gag ttt cag ctc tcc    1512
Ala Val Tyr His Gln Gly His Tyr Glu Trp Ser Glu Phe Gln Leu Ser
 50                  55                  60 ctg atc gcg tcg atc cgc cac tgg gag cag ggc gag gga agg gag ccg    1560
Leu Ile Ala Ser Ile Arg His Trp Glu Gln Gly Glu Gly Arg Glu Pro
 65                  70                  75 tgg agc tac tac gag cac tgg ctc aat gcg ctc gag tcg gta ctc gcc    1608
Trp Ser Tyr Tyr Glu His Trp Leu Asn Ala Leu Glu Ser Val Leu Ala
 80                  85                  90                  95 gcc agc ggc gcc tta tcg gac gca gtg ggc ctc gat gag cgc acg cgc    1656
Ala Ser Gly Ala Leu Ser Asp Ala Val Gly Leu Asp Glu Arg Thr Arg
                 100                 105                 110 gaa gtt ctc acc acc cca cgg aac acg aac cac cac cat gca cat cgc    1704
Glu Val Leu Thr Thr Pro Arg Asn Thr Asn His His His Ala His Arg
             115                 120                 125 gaa ccc gtc gcg atc tca tct gcg gtg aac taa cccgcggcgc tactcgtccg    1757
Glu Pro Val Ala Ile Ser Ser Ala Val Asn
             130                 135
```

```
ctggccagct ctctgcctgc tgtccagcga acgacacctc cgtgacagct tctcgttcac    1817
cgacccgatc actgattccc gacgcggtta ccaacgagca cccgcgtata aacagaaccg    1877
caaaggtatc gcagctgtcg gggacgagcg aatagcggat cgctcgcggg ggccggaccc    1937
atgcagctga tgctgctttc gcccgaatag cccagatatc cactggacga ggtgcgaggc    1997
ccgatacaag gcgagcgtca gcaaccggca aaccacagcg tccagagcca gcaccgtcat    2057
gtctagaaga ggaaagcatt gacgattact accacttcgc caaggcagat cgccggtcgg    2117
tggacacgtg ccgagcggca acgactgagc gctatcatcg gcaccatcgc attgctgcac    2177
gtgctaggta tcgcaatgta tctcgggcgc tcgggtaacc cggccgccgc tggtagcctg    2237
gctggctcgg gactgctcgc ctatgtcctg gtgcgcggc acgcgttcga tgccgaccac    2297
atcgcggcca tcgacgacac caccgcatc atgctccttc gcggacgccg accgtcggc    2357 gtcggattct ttttcgccat ggggcattcg actgtcgtcc tcgttctctc tctgatcgtc    2417
gctttcggag cgggctcgct cagttcgatg gaagcgtccc gggtcgagga gatcggaggt    2477
tacgtcgcga cctgcgtggc agtgctgttc ttggtgctgg tggccgcact caacagtttc    2537
gttctgcgca agctcctcgc tctgtctcgt cggatgcgca ctggggaaga tatctccggc    2597
gacctcgagc gcgggctggg tgaacgggga ttgctcagct ggcttctcag cggccgattg    2657
cgcgggctga ttcgttcgtc ctggcacatg tacccggtgg gcctgctcat gggtctcggc    2717
```

```
ctggaaaccg catccgaagt gacattgctg tctctcactg cctccgcagc gagcggaggt    2777
cagctatcgc taatggcgat tgtgagcctt ccattgttgt ttgccgcggg gatgagcacc    2837
ttcgatactg cagactcact cgtcatgacc cgcgcctatt cgtggtccta taacgatgcc    2897
cagcgccgcc ttcgcttcaa cactgtaacc acgggtgcga ccatggtcat cgggttcttc    2957
gtcgcgggaa tctacgtttc tggactgctt gcgccgctac cagggttcgg ttggctgacc    3017
cctctgggcg cgatcgccga caacttcgag ttcctcggct acgcagtcgc cggattgttc    3077
gttgctacct gggcaatcgc agcactggtt agccggcctc gacggcttgt cggcagctcg    3137
aaggtgtga                                                            3146
```

<210> SEQ ID NO 6
<211> LENGTH: 137
<212> TYPE: PRT
<213> ORGANISM: Rhodococcus opacus

<400> SEQUENCE: 6

```
Val Ser Thr Arg Ile Asp Ala Thr Glu Leu Gly Glu Ala Arg Arg
 1               5                  10                  15

Ile Glu Ala Leu Val Cys Asp Leu Pro Gly Gly Asp Val Gly Ser Arg
            20                  25                  30

Ala Phe Asn Glu Pro Trp Glu Leu Arg Ala Phe Ala Met Ala Val Ala
        35                  40                  45

Val Tyr His Gln Gly His Tyr Glu Trp Ser Glu Phe Gln Leu Ser Leu
    50                  55                  60

Ile Ala Ser Ile Arg His Trp Glu Gln Gly Glu Gly Arg Glu Pro Trp
65                  70                  75                  80

Ser Tyr Tyr Glu His Trp Leu Asn Ala Leu Glu Ser Val Leu Ala Ala
                85                  90                  95

Ser Gly Ala Leu Ser Asp Ala Val Gly Leu Asp Glu Arg Thr Arg Glu
            100                 105                 110

Val Leu Thr Thr Pro Arg Asn Thr Asn His His His Ala His Arg Glu
        115                 120                 125

Pro Val Ala Ile Ser Ser Ala Val Asn
    130                 135
```

<210> SEQ ID NO 7
<211> LENGTH: 17
<212> TYPE: DNA
<213> ORGANISM: Artificial
<220> FEATURE:
<223> OTHER INFORMATION: Primer

<400> SEQUENCE: 7

```
atgaayggha tyttcga                                                   17
```

<210> SEQ ID NO 8
<211> LENGTH: 17
<212> TYPE: DNA
<213> ORGANISM: Artificial
<220> FEATURE:
<223> OTHER INFORMATION: Primer

<400> SEQUENCE: 8

```
atccagtgyy hgtagta                                                   17
```

<210> SEQ ID NO 9
<211> LENGTH: 19
<212> TYPE: DNA

-continued

<210> SEQ ID NO 9  
<211> LENGTH: (continued)  
<212> TYPE: DNA  
<213> ORGANISM: Artificial  
<220> FEATURE:  
<223> OTHER INFORMATION: Primer

<400> SEQUENCE: 9
cgaagacatg atcgtcgtg                                                        19

<210> SEQ ID NO 10  
<211> LENGTH: 16  
<212> TYPE: DNA  
<213> ORGANISM: Artificial  
<220> FEATURE:  
<223> OTHER INFORMATION: Primer

<400> SEQUENCE: 10
accggtccca caccga                                                           16

<210> SEQ ID NO 11  
<211> LENGTH: 16  
<212> TYPE: DNA  
<213> ORGANISM: Artificial  
<220> FEATURE:  
<223> OTHER INFORMATION: Primer

<400> SEQUENCE: 11
tcgaggagat cggagg                                                           16

<210> SEQ ID NO 12  
<211> LENGTH: 18  
<212> TYPE: DNA  
<213> ORGANISM: Artificial  
<220> FEATURE:  
<223> OTHER INFORMATION: Primer

<400> SEQUENCE: 12
gtatcgaagg tgctcatc                                                         18

<210> SEQ ID NO 13  
<211> LENGTH: 15  
<212> TYPE: DNA  
<213> ORGANISM: Artificial  
<220> FEATURE:  
<223> OTHER INFORMATION: Primer

<400> SEQUENCE: 13
cgcgggctgg gtgaa                                                            15

<210> SEQ ID NO 14  
<211> LENGTH: 36  
<212> TYPE: DNA  
<213> ORGANISM: Artificial  
<220> FEATURE:  
<223> OTHER INFORMATION: Primer

<400> SEQUENCE: 14
cggcggaatt caagaaggag acccgcatat gaacgg                                     36

<210> SEQ ID NO 15  
<211> LENGTH: 36  
<212> TYPE: DNA  
<213> ORGANISM: Artificial  
<220> FEATURE:  
<223> OTHER INFORMATION: Primer

<400> SEQUENCE: 15
ggtgcaagct tggatcctgt cagattcctc gagtag                                     36

```
<210> SEQ ID NO 16
<211> LENGTH: 33
<212> TYPE: DNA
<213> ORGANISM: Artificial
<220> FEATURE:
<223> OTHER INFORMATION: Primer

<400> SEQUENCE: 16
gcgaaggatc ctgcatgcat cgaaattaat acg                                33

<210> SEQ ID NO 17
<211> LENGTH: 33
<212> TYPE: DNA
<213> ORGANISM: Artificial
<220> FEATURE:
<223> OTHER INFORMATION: Primer

<400> SEQUENCE: 17
catcaagctt ttcgccatgg ctatatctcc ttc                                33

<210> SEQ ID NO 18
<211> LENGTH: 37
<212> TYPE: DNA
<213> ORGANISM: Artificial
<220> FEATURE:
<223> OTHER INFORMATION: Primer

<400> SEQUENCE: 18
ctgacaggat ccaagaagga gatatagcca tggccga                            37

<210> SEQ ID NO 19
<211> LENGTH: 37
<212> TYPE: DNA
<213> ORGANISM: Artificial
<220> FEATURE:
<223> OTHER INFORMATION: Primer

<400> SEQUENCE: 19
gttgcaagct tggtaccgct caagacatcg cctccct                            37

<210> SEQ ID NO 20
<211> LENGTH: 36
<212> TYPE: DNA
<213> ORGANISM: Artificial
<220> FEATURE:
<223> OTHER INFORMATION: Primer

<400> SEQUENCE: 20
gtgggtacca agaaggaggc gatcatatga gcacgc                             36

<210> SEQ ID NO 21
<211> LENGTH: 32
<212> TYPE: DNA
<213> ORGANISM: Artificial
<220> FEATURE:
<223> OTHER INFORMATION: Primer

<400> SEQUENCE: 21
gcggacgagt agcgaagctt gttagttcac cg                                 32

<210> SEQ ID NO 22
<211> LENGTH: 36
<212> TYPE: DNA
<213> ORGANISM: Artificial
<220> FEATURE:
```

<223> OTHER INFORMATION: Primer

<400> SEQUENCE: 22
tcaaagcttg aaggagatat acatatgacg attact    36

<210> SEQ ID NO 23
<211> LENGTH: 33
<212> TYPE: DNA
<213> ORGANISM: Artificial
<220> FEATURE:
<223> OTHER INFORMATION: Primer

<400> SEQUENCE: 23
gtcaagcttg gtaccgacat ctcacacctt cga    33

<210> SEQ ID NO 24
<211> LENGTH: 6307
<212> TYPE: DNA
<213> ORGANISM: E. coli, Rhodococcus opacus

<400> SEQUENCE: 24

| | | | | |
|---|---|---|---|---|
| aattcttaag aaggagatat | acatatgaac | ggcatcttcg | atctaggcgg | aaccgacggc | 60 |
| atggggccgg tcgacaacga | caaaggcacc | gagccggtgt | tccgctcagc | gtgggaaaag | 120 |
| gccgccttct cgatgttcgc | acaaggcgcc | cgagctggcc | tctacaacat | cgacgagttc | 180 |
| cggcactgcg tcgagcagat | ggaccccgcc | gagtatttac | tatcgaacta | ctacgagcac | 240 |
| tggacgcatg ccgtcgaaca | cttcgcccag | caaaagaacc | tcatcacagc | ggcagagctc | 300 |
| gaaaagcgca cgcatttcta | ccgggataac | ccagaagccc | ccttccgga | gcgcaaggac | 360 |
| ccagagctcc tcgacttcgt | gaacaccgcg | atcgcgaacg | gtttcgcggc | ctcccgtgaa | 420 |
| accaataggt cggcagcatt | caccatcggc | gaccaggtac | tgattgctgc | ggacagtcca | 480 |
| ttcggacaca cccgacgggc | cggctacatc | cgcggtaaga | ccggagtcat | caccgcgaca | 540 |
| cacggcgcct acgtctatcc | cgacaccgcc | ggtaacgggc | tcggtgagtg | cccagagcac | 600 |
| gtctacaccg tgaagttcac | cgccaccgaa | ctttggggcg | aacagagcgg | tgatcgccac | 660 |
| agcaccgtct atttcgatgt | ctgggaaccg | tacctctcgc | tcgctaccgc | accctctact | 720 |
| cgaggaatct gacaggatcc | tgcatgcatc | gaaattaata | cgacgaaatt | aatacgactc | 780 |
| actataggc aattgcgatc | accacaattc | agcaaattgt | gaacatcatc | acgttcatct | 840 |
| ttccctggtt gccaatggcc | catttttcctg | tcagtaacga | gaaggtcgcg | aattcaggcg | 900 |
| cttttttagac tggtcgtaat | gaacaattct | taagaaggag | atatagccat | ggccgaacag | 960 |
| cgcaccgaca cccaattgcg | tacacacgaa | gaagtcgtcg | cccgagtcaa | ggcgctcgag | 1020 |
| gcgctgctga tcgagaaagg | cgtcatgacg | accgaggccg | tcgaccggat | ggccgaggta | 1080 |
| tacgagaacg aagtcggccc | ccagatcggc | gctcagattg | tcgccaaggc | gtggaccgac | 1140 |
| ccgaagttca agaagaggtt | gctggccaat | gccacgactg | cctgcgcaga | gatgggctac | 1200 |
| ggcggtctgc agggcgaaga | catgatcgtc | gtggaaaaca | ccgacaccgt | acacaacgcg | 1260 |
| attgtgtgca ccctctgctc | ctgctacccg | tggccggtct | tgggcctgcc | accgaactgg | 1320 |
| tacaaggcac cggcttaccg | cgcacggatc | gtgcgcgaac | gcggaaggt | cctcgccgag | 1380 |
| gacttcgact ttcccatccc | cgacgacgtc | gagatccgcg | tgtgggactc | gagcgccgag | 1440 |
| ctgcgctatt gggttttacc | gcagcgccct | gcacacaccg | aaagattgac | ggaatccgag | 1500 |
| ctggtagcgc tggtcacccg | cgactcgatg | atcggtgtgg | accggtgag | ggaggcgatg | 1560 |
| tcttgagcgg taccaagaag | gaggcgatca | tatgagcacg | cgcattgacg | caaccgagct | 1620 |

```
cggggaagca cgccggcgaa tcgaggcgtt ggtgtgtgat ctgcccggtg gtgacgtagg    1680
ctcacgcgcc ttcaacgagc cgtgggaatt gcgtgccttc gcgatggccg ttgccgtgta    1740
tcaccagggt cactacgaat ggagtgagtt tcagctctcc ctgatcgcgt cgatccgcca    1800
ctgggagcag ggcgagggaa gggagccgtg gagctactac gagcactggc tcaatgcgct    1860
cgagtcggta ctcgccgcca gcggcgcctt atcggacgca gtgggcctcg atgagcgcac    1920
gcgcgaagtt ctcaccaccc cacggaacac gaaccaccac catgcacatc gcgaacccgt    1980
cgcgatctca tctgcggtga actaacaagc ttggctgttt tggcggatga gagaagattt    2040
tcagcctgat acagattaaa tcagaacgca gaagcggtct gataaaacag aatttgcctg    2100
gcggcagtag cgcggtggtc ccacctgacc ccatgccgaa ctcagaagtg aaacgccgta    2160
gcgccgatgg tagtgtgggg tctccccatg cgagagtagg gaactgccag gcatcaaata    2220
aaacgaaagg ctcagtcgaa agactgggcc tttcgtttta tctgttgttt gtcggtgaac    2280
gctctcctga gtaggacaaa tccgccggga gcggatttga acgttgcgaa gcaacggccc    2340
ggagggtggc gggcaggacg cccgccataa actgccaggc atcaaattaa gcagaaggcc    2400
atcctgacgg atggcctttt tgcgtttcta caaactcttt tgtttatttt tctaaataca    2460
ttcaaatatg tatccgctca tgagacaata accctgataa atgcttcaat aatattgaaa    2520
aaggaagagt atgagtattc aacatttccg tgtcgccctt attccctttt ttgcggcatt    2580
ttgccttcct gttttttgctc acccagaaac gctggtgaaa gtaaaagatg ctgaagatca    2640
gttgggtgca cgagtgggtt acatcgaact ggatctcaac agcggtaaga tccttgagag    2700
ttttcgcccc gaagaacgtt ttccaatgat gagcactttt aaagttctgc tatgtggcgc    2760
ggtattatcc cgtgttgacg ccgggcaaga gcaactcggt cgccgcatac actattctca    2820
gaatgacttg gttgagtact caccagtcac agaaaagcat cttacggatg gcatgacagt    2880
aagagaatta tgcagtgctg ccataaccat gagtgataac actgcggcca acttacttct    2940
gacaacgatc ggaggaccga aggagctaac cgcttttttg cacaacatgg gggatcatgt    3000
aactcgcctt gatcgttggg aaccggagct gaatgaagcc ataccaaacg acgagcgtga    3060
caccacgatg cctgtagcaa tggcaacaac gttgcgcaaa ctattaactg gcgaactact    3120
tactctagct tcccggcaac aattaataga ctggatggag gcggataaag ttgcaggacc    3180
acttctgcgc tcggcccttc cggctggctg gtttattgct gataaatctg gagccggtga    3240
gcgtgggtct cgcggtatca ttgcagcact ggggccagat ggtaagccct cccgtatcgt    3300
agttatctac acgacgggga gtcaggcaac tatggatgaa cgaaatagac agatcgctga    3360
gataggtgcc tcactgatta agcattggta actgtcagac caagtttact catatatact    3420
ttagattgat ttaaaacttc attttaatt taaaaggatc taggtgaaga tccttttga    3480
taatctcatg accaaaatcc cttaacgtga gttttcgttc cactgagcgt cagacccgt    3540
agaaaagatc aaaggatctt cttgagatcc ttttttctg cgcgtaatct gctgcttgca    3600
aacaaaaaaa ccaccgctac cagcggtggt ttgtttgccg gatcaagagc taccaactct    3660
ttttccgaag gtaactggct tcagcagagc gcagatacca atactgtcc ttctagtgta    3720
gccgtagtta ggccaccact tcaagaactc tgtagcaccg cctacatacc tcgctctgct    3780
aatcctgtta ccagtggctg ctgccagtgg cgataagtcg tgtcttaccg ggttggactc    3840
aagacgatag ttaccggata aggcgcagcg gtcgggctga acggggggtt cgtgcacaca    3900
gcccagcttg gagcgaacga cctacaccga actgagatac ctacagcgtg agctatgaga    3960
```

```
aagcgccacg cttcccgaag ggagaaaggc ggacaggtat ccggtaagcg gcagggtcgg    4020
aacaggagag cgcacgaggg agcttccagg gggaaacgcc tggtatcttt atagtcctgt    4080
cgggtttcgc cacctctgac ttgagcgtcg attttgtga tgctcgtcag ggggcggag     4140 cctatggaaa aacgccagca acgcggcctt tttacggttc ctggccttt gctggccttt    4200 tgctcacatg ttctttcctg cgttatcccc tgattctgtg gataaccgta ttaccgcctt    4260
tgagtgagct gataccgctc gccgcagccg aacgaccgag cgcagcgagt cagtgagcga    4320
ggaagcggaa gagcgcctga tgcggtattt tctccttacg catctgtgcg gtatttcaca    4380
ccgcatatat ggtgcactct cagtacaatc tgctctgatg ccgcatagtt aagccagtat    4440
acactccgct atcgctacgt gactgggtca tggctgcgcc ccgacacccg ccaacacccg    4500
ctgacgcgcc ctgacgggct tgtctgctcc cggcatccgc ttacagacaa gctgtgaccg    4560
tctccgggag ctgcatgtgt cagaggtttt caccgtcatc accgaaacgc gcgaggcagc    4620
tgcggtaaag ctcatcagcg tggtcgtgaa gcgattcaca gatgtctgcc tgttcatccg    4680
cgtccagctc gttgagtttc tccagaagcg ttaatgtctg gcttctgata aagcgggcca    4740
tgttaagggc ggttttttcc tgtttggtca cttgatgcct ccgtgtaagg gggaatttct    4800
gttcatgggg gtaatgatac cgatgaaacg agagaggatg ctcacgatac gggttactga    4860
tgatgaacat gcccggttac tggaacgttg tgagggtaaa caactggcgg tatggatgcg    4920
gcgggaccag agaaaaatca ctcagggtca atgccagcgc ttcgttaata cagatgtagg    4980
tgttccacag ggtagccagc agcatcctgc gatgcagatc cggaacataa tggtgcaggg    5040
cgctgacttc gcgtttcca gactttacga aacacggaaa ccgaagacca ttcatgttgt    5100
tgctcaggtc gcagacgttt tgcagcagca gtcgcttcac gttcgctcgc gtatcggtga    5160
ttcattctgc taaccagtaa ggcaacccg ccagcctagc cgggtcctca acgacaggag    5220
cacgatcatg cgcacccgtg gccaggaccc aacgctgccc gagatgcgcc gcgtgcggct    5280
gctggagatg gcggacgcga tggatatgtt ctgccaaggg ttggtttgcg cattcacagt    5340
tctccgcaag aattgattgg ctccaattct tggagtggtg aatccgttag cgaggtgccg    5400
ccggcttcca ttcaggtcga ggtggcccgg ctccatgcac cgcgacgcaa cgcggggagg    5460
cagacaaggt atagggcggc gcctacaatc catgccaacc cgttccatgt gctcgccgag    5520
gcggcataaa tcgccgtgac gatcagcggt ccagtgatcg aagttaggct ggtaagagcc    5580
gcgagcgatc cttgaagctg tccctgatgg tcgtcatcta cctgcctgga cagcatggcc    5640
tgcaacgcgg gcatcccgat gccgccggaa gcgagaagaa tcataatggg gaaggccatc    5700
cagcctcgcg tcgcgaacgc cagcaagacg tagcccagcg cgtcggccgc catgccggcg    5760
ataatggcct gcttctcgcc gaaacgtttg gtggcgggac cagtgacgaa ggcttgagcg    5820
agggcgtgca agattccgaa taccgcaagc gacaggccga tcatcgtcgc gctccagcga    5880
aagcggtcct cgccgaaaat gacccagagc gctgccggca cctgtcctac gagttgcatg    5940
ataaagaaga cagtcataag tgcggcgacg atagtcatgc cccgcgccca ccggaaggag    6000
ctgactgggt tgaaggctct caagggcatc ggtcgacgct ctcccttatg cgactcctgc    6060
attaggaagc agcccagtag taggttgagg ccgttgagca ccgccgccgc aaggaatggt    6120
gcatgcatgc atcgaaatta atacgacgaa attaatacga ctcactatag gcaattgcg    6180 atcaccacaa ttcagcaaat tgtgaacatc atcacgttca tctttccctg gttgccaatg    6240
gcccattttc ctgtcagtaa cgagaaggtc gcgaattcag gcgctttta gactggtcgt    6300 aatgaac                                                             6307
```

-continued

<210> SEQ ID NO 25
<211> LENGTH: 6191
<212> TYPE: DNA
<213> ORGANISM: E. coli, Rhodococcus opacus

<400> SEQUENCE: 25

| | | | | | |
|---|---|---|---|---|---|
| aattcttaag | aaggagatat | acatatgacg | attactacca | cttcgccaag | gcagatcgcc | 60 |
| ggtcggtgga | cacgtgccga | gcggcaacga | ctgagcgcta | tcatcggcac | catcgcattg | 120 |
| ctgcacgtgc | taggtatcgc | aatgtatctc | gggcgctcgg | gtaacccggc | cgccgctggt | 180 |
| agcctggctg | gctcgggact | gctcgcctat | gtcctgggtg | cgcggcacgc | gttcgatgcc | 240 |
| gaccacatcg | cggccatcga | cgacaccacc | cgcatcatgc | tccttcgcgg | acgccgaccc | 300 |
| gtcggcgtcg | gattcttttt | cgccatgggg | cattcgactg | tcgtcctcgt | tctctctctg | 360 |
| atcgtcgctt | tcgagcgggc | tcgctcagt | tcgatggaag | cgtcccgggt | cgaggagatc | 420 |
| ggaggttacg | tcgcgacctg | cgtggcagtg | ctgttcttgg | tgctggtggc | cgcactcaac | 480 |
| agtttcgttc | tgcgcaagct | cctcgctctg | tctcgtcgga | tgcgcactgg | ggaagatatc | 540 |
| tccggcgacc | tcgagcgcgg | gctgggtgaa | cggggattgc | tcagctggct | tctcagcggc | 600 |
| cgattgcgcg | ggctgattcg | ttcgtcctgg | cacatgtacc | cggtgggcct | gctcatgggt | 660 |
| ctcggcctgg | aaaccgcatc | cgaagtgaca | ttgctgtctc | tcactgcctc | cgcagcgagc | 720 |
| ggaggtcagc | tatcgctaat | ggcgattgtg | agccttccat | tgttgtttgc | cgcggggatg | 780 |
| agcaccttcg | atactgcaga | ctcactcgtc | atgacccgcg | cctattcgtg | gtcctataac | 840 |
| gatgcccagc | gccgcttcg | cttcaacact | gtaaccacgg | gtgcgaccat | ggtcatcggg | 900 |
| ttcttcgtcg | cgggaatcta | cgtttctgga | ctgcttgcgc | cgctaccagg | gttcggttgg | 960 |
| ctgaccctc | tgggcgcgat | cgccgacaac | ttcgagttcc | tcggctacgc | agtcgccgga | 1020 |
| ttgttcgttg | ctacctgggc | aatcgcagca | ctggttagcc | ggcctcgacg | gcttgtcggc | 1080 |
| agctcgaagg | tgtgagatgt | cggtaccaag | cttggctgtt | ttggcggatg | agagaagatt | 1140 |
| tcagcctga | tacagattaa | atcagaacgc | agaagcggtc | tgataaaaca | gaatttgcct | 1200 |
| ggcggcagta | gcgcggtggt | cccacctgac | cccatgccga | actcagaagt | gaaacgccgt | 1260 |
| agcgccgatg | gtagtgtggg | gtctccccat | gcgagagtag | ggaactgcca | ggcatcaaat | 1320 |
| aaaacgaaag | gctcagtcga | aagactgggc | ctttcgtttt | atctgttgtt | tgtcggtgaa | 1380 |
| cgctctcctg | agtaggacaa | atccgccggg | agcggatttg | aacgttgcga | agcaacggcc | 1440 |
| cggagggtgg | cgggcaggac | gcccgccata | aactgccagg | catcaaatta | agcagaaggc | 1500 |
| catcctgacg | gatggccttt | ttgcgtttct | acaaactctt | ttgtttattt | ttctaaatac | 1560 |
| attcaaatat | gtatccgctc | atgagacaat | aaccctgata | aatgcttcaa | taatatcgtc | 1620 |
| cattccgaca | gcatcgccag | tcactatggc | gtgctgctag | cgctatatgc | gttgatgcaa | 1680 |
| tttctatgcg | cacccgttct | cggagcactg | tccgaccgct | ttggccgccg | cccagtcctg | 1740 |
| ctcgcttcgc | tacttggagc | cactatcgac | tacgcgatca | tggcgaccac | acccgtcctg | 1800 |
| tggatcctct | acgccggacg | catcgtggcc | ggcatcaccg | gcgccacagg | tgcggttgct | 1860 |
| ggcgcctata | tcgccgacat | caccgatggg | gaagatcggg | ctcgccactt | cgggctcatg | 1920 |
| agcgcttgtt | tcggcgtggg | tatggtggca | ggccccgtgg | ccgggggact | gttgggcgcc | 1980 |
| atctccttgc | atgcaccatt | ccttgcggcg | gcggtgctca | acggcctcaa | cctactactg | 2040 |
| ggctgcttcc | taatgcagga | gtcgcataag | ggagagcgtc | gaccgatgcc | cttgagagcc | 2100 |

```
ttcaacccag tcagctcctt ccggtgggcg cggggcatga ctatcgtcgc cgcacttatg    2160
actgtcttct ttatcatgca actcgtagga caggtgccgg cagcgctctg ggtcattttc    2220
ggcgaggacc gctttcgctg gagcgcgacg atgatcggcc tgtcgcttgc ggtattcgga    2280
atcttgcacg ccctcgctca agccttcgtc actggtcccg ccaccaaacg tttcggcgag    2340
aagcaggcca ttatcgccgg catggcggcc gacgcgctgg gctacgtctt gctggcgttc    2400
gcgacgcgag gctggatggc cttccccatt atgattcttc tcgcttccgg cggcatcggg    2460
atgcccgcgt tgcaggccat gctgtccagg caggtagatg acgaccatca gggacagctt    2520
caaggatcgc tcgcggctct taccagccta acttcgatca ctggaccgct gatcgtcacg    2580
gcgatttatg ccgcctcggc gagcacatgg aacgggttgg catggattgt aggcgccgcc    2640
ctataccttg tctgcctccc cgcgttgcgt cgcggtgcat ggagccgggc cacctcgacc    2700
tgaatggaag ccggcggcac ctcgctaacg gattcaccac tccaagaatt ggagccaatc    2760
aattcttgcg gagaactgtg aatgcgcaaa ccaacccttg gcagaacata tccatcgcgt    2820
ccgccatctc cagcagccgc acgcggcgca tctcgggcag cgttgggtcc tggccacggg    2880
tgcgcatgat cgtgctcctg tcgttgagga cccggctagg ctggcggggt tgccttactg    2940
gttagcagaa tgaatcaccg atacgcgagc gaacgtgaag cgactgctgc tgcaaaacgt    3000
ctgcgacctg agcaacaaca tgaatggtct tcggtttccg tgtttcgtaa agtctggaaa    3060
cgcggaagtc ccctacgtgc tgctgaagtt gcccgcaaca gagagtggaa ccaaccggtg    3120
ataccacgat actatgactg agagtcaacg ccatgagcgg cctcatttct tattctgagt    3180
tacaacagtc cgcaccgctg tccggtagct ccttccggtg ggcgcggggc atgactatcg    3240
tcgccgcact tatgactgtc ttctttatca tgcaactcgt aggacaggtg ccggcagcgc    3300
ccaacagtcc cccggccacg gggcctgcca ccatacccac gccgaaacaa gcgccctgca    3360
ccattatgtt ccggatctgc atcgcaggat gctgctggct accctgtgga acacctacat    3420
ctgtattaac gaagcgctaa ccgttttat caggctctgg gaggcagaat aaatgatcat    3480
atcgtcaatt attacctcca cggggagagc ctgagcaaac tggcctcagg catttgagaa    3540
gcacacggtc acactgcttc cggtagtcaa taaaccggta aaccagcaat agacataagc    3600
ggctatttaa cgaccctgcc ctgaaccgac gaccgggtcg aatttgcttt cgaatttctg    3660
ccattcatcc gcttattatc acttattcag gcgtagcacc aggcgtttaa gggcaccaat    3720
aactgcctta aaaaaattac gccccgcccct gccactcatc gcagtactgt tgtaattcat    3780
taagcattct gccgacatgg aagccatcac agacggcatg atgaacctga atcgccagcg    3840
gcatcagcac cttgtcgcct tgcgtataat atttgcccat ggtgaaaacg ggggcgaaga    3900
agttgtccat attggccacg tttaaatcaa aactggtgaa actcacccag ggattggctg    3960
agacgaaaaa catattctca ataaaccctt tagggaaata ggccaggttt tcaccgtaac    4020
acgccacatc ttgcgaatat atgtgtagaa actgccggaa atcgtcgtgg tattcactcc    4080
agagcgatga aaacgtttca gtttgctcat ggaaaacggt gtaacaaggg tgaacactat    4140
cccatatcac cagctcaccg tctttcattg ccatacgaat tccggatgag cattcatcag    4200
gcgggcaaga atgtgaataa aggccggata aaacttgtgc ttatttttct ttacggtctt    4260
taaaaaggcc gtaatatcca gctgaacggt ctggttatag gtacattgag caactgactg    4320
aaatgcctca aaatgttctt tacgatgcca ttgggatata tcaacggtgg tatatccagt    4380
gatttttttc tccattttag cttccttagc tcctgaaaat ctcgataact caaaaaatac    4440
gcccggtagt gatcttattt cattatggtg aaagttggaa cctcttacgt gccgatcaac    4500
```

```
gtctcatttt cgccaaaagt tggcccaggg cttcccggta tcaacaggga caccaggatt    4560
tatttattct gcgaagtgat cttccgtcac aggtatttat tcggcgcaaa gtgcgtcggg    4620
tgatgctgcc aacttactga tttagtgtat gatggtgttt ttgaggtgct ccagtggctt    4680
ctgtttctat cagctgtccc tcctgttcag ctactgacgg ggtggtgcgt aacggcaaaa    4740
gcaccgccgg acatcagcgc tagcggagtg tatactggct tactatgttg gcactgatga    4800
gggtgtcagt gaagtgcttc atgtggcagg agaaaaaagg ctgcaccggt gcgtcagcag    4860
aatatgtgat acaggatata ttccgcttcc tcgctcactg actcgctacg ctcggtcgtt    4920
cgactgcggc gagcggaaat ggcttacgaa cggggcggag atttcctgga agatgccagg    4980
aagatactta acagggaagt gagagggccg cggcaaagcc gtttttccat aggctccgcc    5040
cccctgacaa gcatcacgaa atctgacgct caaatcagtg gtggcgaaac ccgacaggac    5100
tataaagata ccaggcgttt ccctggcgg ctccctcgtg cgctctcctg ttcctgcctt    5160
tcggtttacc ggtgtcattc cgctgttatg ccgcgtttg tctcattcca cgcctgacac    5220
tcagttccgg gtaggcagtt cgctccaagc tggactgtat gcacgaaccc ccgttcagt    5280
ccgaccgctg cgccttatcc ggtaactatc gtcttgagtc caacccggaa agacatgcaa    5340
aagcaccact ggcagcagcc actggtaatt gatttagagg agttagtctt gaagtcatgc    5400
gccggttaag gctaaactga aaggacaagt tttggtgact gcgctcctcc aagccagtta    5460
cctcggttca aagagttggt agctcagaga accttcgaaa aaccgccctg caaggcggtt    5520
ttttcgtttt cagagcaaga gattacgcgc agaccaaaac gatctcaaga agatcatctt    5580
attaagcttg catgcctgca ggacggatcc ccgggtaccg agctcgaatt taatcagata    5640
aaatatttca agatttcagt gcaatttatc tcttcaaatg tagcacctga agtcagcccc    5700
atacgatata agttgtaatt ctcatgtttg acagcttatc atcgataagc tttaatgcgg    5760
tagtttatca cagttaaatt gctaacgcag tcaggcaccg tgtatgaaat ctaacaatgc    5820
gctcatcgtc atcctcggca ccgtcaccct ggatgctgta ggcataggct tggttatgcc    5880
ggtactgccg ggcctcttgc gggattagtc atgccccgcg cccaccggaa ggagctgact    5940
gggttgaagg ctctcaaggg catcggtcga cgctctccct tatgcgactc ctgcattagg    6000
aagcagccca gtagtaggtt gaggccgttg agcaccgccg ccgcaaggaa tggtgcatgc    6060
atcgatcacc acaattcagc aaattgtgaa catcatcacg ttcatctttc cctggttgcc    6120
aatgcccat  tttcctgtca gtaacgagaa ggtcgcgaat tcaggcgctt tttagactgg    6180
tcgtaatgaa c                                                          6191
```